US006864389B2

(12) United States Patent
Okuda et al.

(10) Patent No.: US 6,864,389 B2
(45) Date of Patent: Mar. 8, 2005

(54) METHOD FOR PRODUCING α-HYDROXYCARBOXYLIC ACID

(75) Inventors: Norimasa Okuda, Ibaraki (JP); Hisashi Semba, Ibaraki (JP); Yukio Dobashi, Ibaraki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/870,483

(22) Filed: Jun. 1, 2001

(65) Prior Publication Data

US 2003/0171614 A1 Sep. 11, 2003

(30) Foreign Application Priority Data

| Jun. 2, 2000 | (JP) | 2000-166382 |
| Jun. 7, 2000 | (JP) | 2000-171186 |
| Nov. 17, 2000 | (JP) | 2000-350695 |

(51) Int. Cl.⁷ .................. C07B 57/00; C07C 65/21; C07C 59/00; C07C 51/42; C12P 7/42
(52) U.S. Cl. ............... 562/401; 562/579; 562/580; 562/470; 435/146
(58) Field of Search ............... 562/470, 579, 562/580, 401, 459; 435/146

(56) References Cited

U.S. PATENT DOCUMENTS

| 4,218,380 A | * | 8/1980 | Fiege et al. ............. 549/436 |
| 4,351,955 A | | 9/1982 | Willis et al. |
| 4,694,090 A | * | 9/1987 | Shiono et al. ............ 549/407 |
| 4,945,180 A | | 7/1990 | Schäfer |
| 5,763,652 A | * | 6/1998 | Kawabe et al. ............ 562/512 |
| 2001/0041359 A1 | | 11/2001 | Pochlauer et al. |

FOREIGN PATENT DOCUMENTS

| DE | 2 228 641 A1 | 4/1973 |
| EP | 0 293 752 A3 | 12/1988 |
| EP | 0 293 752 A2 | 12/1988 |
| EP | 0 293 752 A | 12/1998 |
| EP | 1 148 042 A | 10/2001 |
| EP | 1 148 042 A2 | 10/2001 |
| FR | 2 156 791 | 6/1973 |
| JP | 02-229135 | 9/1990 |
| JP | 04-193845 | 7/1992 |
| JP | 1005985 | 3/1998 |
| JP | 10-059895 | * 3/1998 |
| WO | WO 02/22546 A1 | 3/2002 |

OTHER PUBLICATIONS

Effenberger et al. "Enzyme–Catalyzed Synthesis of (R) —Ketone–Cyanohydrins and Their Hydrolysis to (R) –α Hydroxy α–Methyl–Carboxylic Acids," *Tetrahedron Letters*, vol. 32 (23): 2605–2608 (1991).

Ziegler et al. "Ein einfacher Zugang zu (R)– α –Hydrocarbonsauren und (R)–1–Amino–2–alkoholen aus (R)–Cyanohydrinen," *Synthesis*, pp. 575–578 (1990), with English Abstract.

Effenberger, Franz et al. "Enzyme–Catalyzed Synthesis of (R)–Ketone–Cyanohydrins and Their Hydrolysis to (R)–α–Methyl–Carboxylic Acids," *Tetrahedron Letters*, 32(23): 2605–2608 (1991).

Effenberger, Franz, "Enzyme–Catalyzed Preparation and Synthetic Applications of Optically Active Cyanohydrins," *Chimia*, 53(12): 3–10 (1999).

Zeigler, Thomas et al., "Ein einfacher Zugang zu (R)–α–Hydroxycarbonsäuren und (R)–1–Amino–2–alkoholen aus (R)–Cyanhydrinen." *Synthesis*, pp. 575–578 (1990).

European Search Report, for corresponding EP 01304812.9, dated Sep. 25, 2002.

Partial European Search Report, for corresponding European Patent Application No. 01304812.9–2103, dated Jul. 10, 2002.

Braun, Robert D., *Introduction to Instrumental Analysis, Chapter 25 —Liquid Chromatography*, McGraw–Hill Book Company, pp. 839–840 (1987).

Effenberger et al., "Enzyme–catalyzed synthesis of (S)–cyanohydrins and subsequent hydrolysis to (S)–alpha–hydroxy–carboxylic acids," *Tetrahedron Letters*, 31(9):1249–1252 (1990).

* cited by examiner

Primary Examiner—Cecilia J. Tsang
Assistant Examiner—Taylor V. Oh
(74) Attorney, Agent, or Firm—Finnegan, Henderson, Farabow, Garrett & Dunner

(57) ABSTRACT

The present invention relates to:
a method for producing α-hydroxycarboxylic acid, which comprises hydrolyzing cyanohydrin in the presence of a hydrocarbon solvent;
a method for producing optically active α-hydroxycarboxylic acid, which comprises: producing optically active cyanohydrin by performing a reaction between a carbonyl compound and hydrogen cyanide, using a solvent comprising at least one organic solvent selected from a group consisting of an alcoholic solvent, an ester solvent, an ethereal solvent and a carboxylic solvent; removing said organic solvent from said reaction solvent; and hydrolyzing the remaining reaction mixture without isolating optically active cyanohydrin;
a method for producing optically active α-hydroxycarboxylic acid, which comprises hydrolyzing optically active cyanohydrin, using at most 10 equivalents of mineral acid relative to said optically active cyanohydrin under the condition that maximum temperature when reacting is 90° C. or less; and
a method for producing optically active crystalline α-hydroxycarboxylic acid, which comprises crystallizing optically active α-hydroxycarboxylic acid in an aqueous solution.

23 Claims, No Drawings

SEQUENCE LISTING

```
<160> NUMBER OF SEQ ID NOS: 2
<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
ggggaattca tggtaactgc acattttgtt ctgattc                                 37

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
ggggtcgacc tcacggatta gaagccgccg                                         30
```

METHOD FOR PRODUCING α-HYDROXYCARBOXYLIC ACID

BACKGROUND OF THE INVENTION

The present invention relates to a method for producing α-hydroxycarboxylic acid and optically active α-hydroxycarboxylic acid, both of which are useful as a pharmaceutical intermediate or the like.

As a method for producing α-hydroxycarboxylic acid, hydrolysis of cyanohydrin is known. Such hydrolysis is generally carried out in an aqueous solvent containing cyanohydrin and an acid catalyst (e.g. concentrated hydrochloric acid), after hydrolysis, the reaction solution is a single solution.

However, for the above hydrolysis reaction, there are some problems in that the reaction solution becomes dark brown due to the generation of a colored substance, or the removal of by-products is difficult, resulting in the difficulty of obtaining of a good yield of high purity α-hydroxycarboxylic acid.

Furthermore, optically active α-hydroxycarboxylic acid have previously been produced by a method, which comprises: obtaining optically active cyanohydrin by the asymmetric addition of hydrogen cyanide to a corresponding carbonyl compound in an organic solvent such as an alcoholic solvent, an ester solvent, an ethereal solvent, a carboxylic solvent and a hydrocarbon-based solvent, in the presence of enzymes such as (S)-hydroxynitrilelyase and (R)-hydroxynitrilelyase extracted from plants or enzymes produced by a gene recombinant microorganism, into which a gene of those enzymes is incorporated; and hydrolyzing the obtained optically active cyanohydrin (e.g. *Synthesis*, July 1990, 575–578; *Tetrahedron Letters*, 32, 2605–2608 (1991); Japanese Patent Application filed Nos. 63-219388 and 5-317065; WO98/30711).

In these methods, hydrolysis is performed after the isolation of optically active cyanohydrin, or in consideration of efficiency, hydrolysis is performed without the removal of the reaction solvent used in the production process of the optically active cyanohydrin.

The known methods for synthesizing optically active α-hydroxycarboxylic acid by hydrolysis of optically active cyanohydrin include, for example, a method described in *Synthesis*, July 1990, 575–578 and a method described in *Tetrahedron Letters*, 32, 2605–2608 (1991), wherein reaction with concentrated hydrochloric acid at room temperature is followed by reaction at reflux temperature.

With regard to these methods, however, since a large amount of hydrochloric acid, about 30 times the amount of cyanohydrin by molar ratio is used, industrial application of these methods involves many disadvantages such as the high-cost raw materials, low productivity related to the necessity of a huge reactor, a large amount of waste liquid and so on. Furthermore, for the reason that generally α-hydroxycarboxylic acid of interest is highly soluble in water, in a case where, after reaction with a large amount of acid, the substance is purified by operations such as extraction or crystallization, a large amount of substance may disadvantageously remain in aqueous solution, having low yield.

Still more, where inappropriate reaction conditions are applied to a reaction, a side reaction or racemization reaction may often occur, resulting in a low yield and low optical purity of α-hydroxycarboxylic acid.

OBJECTS AND SUMMARY OF THE INVENTION

The object of the first aspect of the present invention is to provide a method for producing high purity α-hydroxycarboxylic acid.

The object of the second and third aspects of the present invention is to provide an industrially advantageous method for producing optically active α-hydroxycarboxylic acid.

As a result of thorough studies by the present inventors directed toward the object of the first aspect above, we have found that the object can be achieved by hydrolyzing cyanohydrin in the presence of a hydrocarbon solvent, thereby completing the first aspect of the present invention.

That is to say, the first aspect of the present invention comprises the following features of invention.

(1) A method for producing α-hydroxycarboxylic acid, which comprises hydrolyzing cyanohydrin in the presence of a hydrocarbon solvent.

(2) The method for producing α-hydroxycarboxylic acid according to (1) above, which comprises separating and removing the hydrocarbon solvent phase from a reaction solution after hydrolysis reaction.

(3) The method for producing α-hydroxycarboxylic acid according to (1) or (2) above, wherein the hydrolysis reaction is carried out using mineral acid.

Moreover, as a result of thorough studies by the present inventors to improve the yield and optical purity of optically active α-hydroxycarboxylic acid, we have found that, in a case where an alcoholic solvent, an ester solvent, an ethereal solvent, a carboxylic solvent or a hydrocarbon-based solvent is used as a reaction solvent in the production process of optically active cyanohydrin, followed by the removal of the solvent and hydrolysis, both the yield and optical purity of optically active α-hydroxycarboxylic acid are improved, compared with a case where hydrolysis is performed without removing the solvent; thereby completing the second aspect of the present invention.

That is to say, the second aspect of the present invention comprises the following features of invention.

(1) A method for producing optically active α-hydroxycarboxylic acid, which comprises: producing optically active cyanohydrin by performing a reaction between a carbonyl compound and hydrogen cyanide, using a solvent comprising at least one organic solvent selected from a group consisting of an alcoholic solvent, an ester solvent, an ethereal solvent and a carboxylic solvent; removing the above organic solvent from the above reaction solvent; and hydrolyzing the remaining reaction mixture without isolating optically active cyanohydrin.

(2) The method for producing optically active α-hydroxycarboxylic acid according to (1) above, wherein the amount of the above organic solvent in the reaction mixture subjected to hydrolysis is less than 10 weight %.

(3) The method for producing optically active α-hydroxycarboxylic acid according to (1) or (2) above, wherein the hydrolysis reaction is carried out using mineral acid.

As a result of further thorough studies by the present inventors directed toward the object of the third aspect of the present invention, we have found that the object can be achieved by hydrolyzing optically active cyanohydrin, using at most 10 equivalents of mineral acid relative to the above optically active cyanohydrin under the condition that maximum temperature on reaction time is 90° C. or less; thereby completing the third aspect of the present invention.

That is to say, the third aspect of the present invention comprises the following feature of invention.
(1) A method for producing optically active α-hydroxycarboxylic acid, which comprises hydrolyzing optically active cyanohydrin, using at most 10 equivalents of mineral acid relative to said optically active cyanohydrin under the condition that maximum temperature on reaction time is 90° C. or less.

Furthermore, the present inventors have found that the crystal with high packing density of optically active α-hydroxycarboxylic acid can be obtained by crystallizing optically active α-hydroxycarboxylic acid in an aqueous solution, thereby completing a fourth aspect of the present invention.

That is to say, the fourth aspect of the present invention comprises the following features of invention.
(1) A method for producing optically active crystalline α-hydroxycarboxylic acid, which comprises crystallizing optically active α-hydroxycarboxylic acid in an aqueous solution.
(2) The method for producing optically active crystalline α-hydroxycarboxylic acid according to (1) above, which comprises crystallizing optically active α-hydroxycarboxylic acid in the presence of a non-miscible organic solvent.
(3) An optically active crystalline chloromandelic acid, which is obtained by the production method according to (1) or (2) above.
(4) A method for producing optically active crystalline α-hydroxycarboxylic acid, which comprises crystallizing the optically active α-hydroxycarboxylic acid obtained by the method according to the first, second or third aspect of the present invention, in an aqueous solution.

The method of the first aspect of the present invention is to produce α-hydroxycarboxylic acid by hydrolyzing cyanohydrin in the presence of a hydrocarbon solvent and converting the cyano group of the above cyanohydrin into a carboxyl group, and according to the present method, it becomes possible to easily remove colored substances and by-products generated during the hydrolysis reaction, resulting in the simple production of high purity α-hydroxycarboxylic acid.

In the first aspect of the present invention, cyanohydrin used as a material for the present invention is not particularly limited, as long as it has, in a molecule thereof, at least one pair consisting of a hydroxyl group and a cyano group which bind to an identical carbon atom.

An example of cyanohydrin used for the present invention includes the compound shown in the following formula (I):

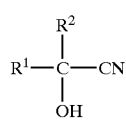
(I)

wherein
$R^1$ and $R^2$ may be different from or identical to each other, independently representing a hydrogen atom, a halogen atom, an amino group, an amino group mono- or di-substituted with a monovalent hydrocarbon group containing at most 14 carbon atoms, a mercapto group or a monovalent hydrocarbon group containing at most 22 carbon atoms, in the above hydrocarbon group, each of —$CH_2$— and $CH_2$ in —$CH_3$ may be substituted with a carbonyl group, a sulfonyl group, —O— or —S—, =$CH_2$ may be substituted with =O or =S; or C—H in —$CH_2$—, C—H in —$CH_3$, C—H in >CH—, C—H in =CH— and C—H in =$CH_2$ may be substituted with N or C-halogen, or
$R^1$ and $R^2$ may together form a divalent group.

The monovalent hydrocarbon group containing at most 22 carbon atoms in the above formula (I) includes a linear or branched chain hydrocarbon group, a monocyclic hydrocarbon group with or without side chain, a polycyclic hydrocarbon group with or without side chain, a spiro hydrocarbon group with or without side chain, a ring-assembled structural hydrocarbon group with or without side chain, or a chain hydrocarbon group with the above cyclic-hydrocarbon. It includes any saturated or unsaturated hydrocarbon group, with the exception that unsaturated hydrocarbon groups having an allene structure (C=C=C) are excluded. The linear or branched chain hydrocarbon group includes, for example, saturated chain hydrocarbon groups such as a linear alkyl group containing at least 1 carbon atom and a branched alkyl group containing at least 3 carbon atoms; unsaturated chain hydrocarbon groups such as a linear alkenyl group containing at least 2 carbon atoms, a branched alkenyl group containing at least 3 carbon atoms, a linear alkynyl group containing at least 3 carbon atoms, a branched alkynyl group containing at least 4 carbon atoms, a linear alkadienyl group containing at least 4 carbon atoms and a branched alkadienyl group containing at least 5 carbon atoms. The monocyclic hydrocarbon group includes, for example, saturated monocyclic hydrocarbon groups such as a cycloalkyl group without side chain which contains at least 3 carbon atoms and a cycloalkyl group with side chain which contains at least 4 carbon atoms in total; unsaturated monocyclic hydrocarbon groups such as a cycloalkenyl group without side chain which contains at least 4 carbon atoms, a cycloalkynyl group with side chain which contains at least 5 carbon atoms in total, a cycloalkadienyl group without side chain which contains at least 5 carbon atoms and a cycloalkadienyl group with side chain which contains at least 6 carbon atoms in total. The unsaturated monocyclic or polycyclic hydrocarbon group includes an aromatic hydrocarbon group including: an aromatic group without side chain which contains 6 to 22 carbon atoms in total such as a phenyl group, a 1-naphthyl group, a 2-naphthyl group and a 9-anthryl group; an aromatic group with side chain which contains at least 7 carbon atoms in total; a phenylphenyl group containing 12 carbon atoms and a phenylphenyl group with side chain which contains at least 13 carbon atoms in total, which are also included in a ring-assembled structural hydrocarbon group. The polycyclic hydrocarbon group includes a condensed cyclic hydrocarbon group without side chain which contains at least 6 carbon atoms, a condensed cyclic hydrocarbon group with side chain which contains at least 7 carbon atoms in total, a bridged cyclic hydrocarbon group with out side chain which contains at least 7 carbon atoms, a bridged cyclic hydrocarbon group with side chain which contains at least 8 carbon atoms in total, a spiro hydrocarbon group without side chain which contains at least 9 carbon atoms in total and a spiro hydrocarbon group with side chain which contains at least 10 carbon atoms in total. In addition, the above condensed cyclic hydrocarbon group without side chain includes those which contain at least 9 carbon atoms in total when one of its condensed rings is a benzene ring, and the above condensed cyclic hydrocarbon group with side chain includes those which contain at least 10 carbon atoms in total when one of its condensed rings is benzene ring. The ring-assembled structural hydrocarbon group includes a cycloalkyl-cycloalkyl group without side chain which contains at least 6 carbon atoms in total, a cycloalkyl-cycloalkyl group with side chain which contains at least 7 carbon atoms in total, a cycloalkylidene-cycloalkyl group without side chain which contains at least 6 carbon atoms in total and a cycloalkylidene-cycloalkyl group with side chain which contains at least 7 carbon atoms in total. "A cyclic hydrocarbon with side chain" in these cyclic hydrocarbons, corresponds to one having a chain hydrocarbon group attached to its ring. Such chain hydrocarbon group having a cyclic hydrocarbon includes a linear alkyl group which is substituted with an aromatic group without side chain and contains at least 7 carbon atoms in total, a linear alkyl group which is substituted with an aromatic group with side chain and contains at least 8 carbon atoms in total, a branched alkyl group which is substituted with an aromatic group without side chain and contains at least 9 carbon atoms in total, a branched alkyl group which is substituted with an aromatic group with side chain and contains at least 10 carbon atoms in total, a linear alkenyl group which is substituted with an aromatic group without side chain and contains at least 8 carbon atoms in total, a linear alkenyl group which is substituted with an aromatic group with side chain and contains at least 9 carbon atoms in total, a branched alkenyl group which is substituted with an aromatic group without side chain and contains at least 9 carbon atoms in total, a branched alkenyl group which is substituted with an aromatic group with side chain and contains at least 10 carbon atoms in total, a linear alkynyl group which is substituted with an aromatic group without side chain and contains at least 8 carbon atoms in total, a linear alkynyl group which is substituted with an aromatic group with side chain and contains at least 9 carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least 4 carbon atoms in total, a linear alkyl group which is substituted with a cycloalkyl group with side chain and contains at least 5 carbon atoms in total, a branched alkyl group which is substituted with a cycloalkyl group without side chain and contains at least 6 carbon atoms in total, a branched alkyl group which is substituted with a cycloalkyl group with side chain and contains at least 7 carbon atoms in total, a linear alkenyl group which is substituted with a cycloalkyl group without side chain and contains at least 5 carbon atoms in total, a linear alkenyl group which is substituted with a cycloalkyl group with side chain and contains at least 6 carbon atoms in total, a branched alkenyl group which is substituted with a cycloalkyl group without side chain and contains at least 6 carbon atoms in total, a branched alkenyl group which is substituted with a cycloalkyl group with side chain and contains at least 7 carbon atoms in total, a linear alkynyl group which is substituted with a cycloalkyl group without side chain and contains at least 5 carbon atoms in total, a linear alkynyl group which is substituted with a cycloalkyl group with side chain and contains at least 6 carbon atoms in total, a branched alkynyl group which is substituted with a cycloalkyl group without side chain and contains at least 7 carbon atoms in total, a branched alkynyl group which is substituted with a cycloalkyl group with side chain and contains at least 8 carbon atoms in total, a branched alkadienyl group which is substituted with a cycloalkyl group without side chain and contains at least 8 carbon atoms in total, a branched alkadienyl group which is substituted with a cycloalkyl group with side chain and contains at least 9 carbon atoms in total.

Hereinafter, each of an aromatic group without side chain, an aromatic group with side chain, and a phenylphenyl group or a phenylphenyl group with side chain, is referred as an aryl group, and a linear or branched alkyl group substituted with the aryl group or groups is referred as an aralkyl group. Other cyclic hydrocarbon groups referring to both one having side chains on its ring and one having no side chains, are simply referred as, for example, cycloalkyl groups, unless otherwise specified. Also, chain hydrocarbon groups referring to both linear one and branched one are simply referred as, for example, alkyl groups.

When —CH$_2$— in the above hydrocarbon group is substituted with a carbonyl group, sulfonyl group, —O— or —S—, a ketone, sulfone, ether or thioether structure is introduced therein, respectively. When —CH$_2$— in —CH$_3$ is substituted with a carbonyl group, —O— or —S—, it converts into a formyl (aldehyde) group, a hydroxyl group or a mercapto group, respectively. When a terminal =CH$_2$ is substituted with =O or =S, a ketone or thioketone structure is introduced therein. When each C—H in —CH$_2$— is substituted with N, it converts into —NH—. When C—H in >CH— is substituted with N, it converts into >N—. When C—H in =CH— is substituted with N, it converts into =N—. When C—H in a terminal —CH$_3$ is substituted with N, —NH$_2$ is introduced therein. When C—H in =CH$_2$ is substituted with N, it converts into =NH. Further, each C—H in —CH$_3$, —CH$_2$—, =CH—, ≡CH or >CH— is substituted with a C-halogen, the carbon is substituted with a halogen atom. The substitution of carbon chains with —O—, —S— or N corresponds to oxa-, thia- or aza-substitution of the hydrocarbon group, respectively. For example, when these substitution take place in a ring carbon of the hydrocarbon ring, the hydrocarbon ring converts into a heterocyclic ring respectively containing oxygen, sulfur or nitrogen. The substitution of CH$_2$ and C—H in the hydrocarbon group may independently take place and it may further take place when CH$_2$ or C—H still remains on the carbon after the prior substitution. Further, the above substitutions may bring the conversion of —CH$_2$—CH$_3$ into —CO—O—H, a carboxylic acid structure.

A halogen atom, herein, refers to a fluorine atom, a chlorine atom, a bromine atom and an iodine atom, but a fluorine atom, a chlorine atom and a bromine atom are preferable.

Accordingly, the above hydrocarbon group may be selected from any chain hydrocarbon group and hydrocarbon group having ring-structured hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include a methyl group, an ethyl group, a propyl group, an isopropyl group, a butyl group, a 1-methylpropyl group, a pentyl group, a 1-methylbutyl group, a hexyl group, a 1-methylpentyl group, a heptyl group, a 1-methylhexyl group, a 1-ethylpentyl group, an octyl group, a nonyl group, a decyl group, an undecyl group, a dodecyl group, a tridecyl group, a tetradecyl group, a 2-methylpropyl group, a 2-methylbutyl group, a 3-methylbutyl group, a 2-methylpentyl group, a 3-methylpentyl group, a 4-methylpentyl group, a methylhexyl group, a methylheptyl group, a methyloctyl group, a methylnonyl group, a 1,1-dimethylethyl group, a 1,1-dimethylpropyl group, a 2,6-dimethylheptyl group, a 3,7-dimethyloctyl group and a 2-ethylhexyl group; cycloalkylalkyl groups include a cyclopentylmethyl group and a cyclohexylmethyl group; cycloalkyl groups include a cyclopropyl group, a cyclobutyl group, a cyclopentyl group, a methylcyclopentyl group, a cyclohexyl group, a methylcyclohexyl group, a cycloheptyl group and a cyclooctyl group; and bicycloalkyl groups include a norbornyl group, a bicyclo [2.2.2] octyl group and an adamantyl group.

The linear or branched alkenyl groups include a vinyl group, an allyl group, a crotyl group (a 2-butenyl group) and an isopropenyl group (a 1-methylvinyl group); cycloalkenyl or cycloalkadienyl groups include a cyclopentenyl group, a cyclopentadienyl group, a cyclohexenyl group and a cyclohexadienyl group.

The linear or branched alkynyl groups include an ethynyl group, a propynyl group and a butynyl group. The aryl groups include a phenyl group, a 1-naphthyl group, a 2-naphthyl group, a 2-phenylphenyl group, a 3-phenylphenyl group, a 4-phenylphenyl group, a 9-anthryl group, a methylphenyl group, a dimethylphenyl group, a trimethylphenyl group, an ethylphenyl group, a methylethylphenyl group, a diethylphenyl group, a propylphenyl group and a butylphenyl group.

The aralkyl groups include a benzyl group, a 1-naphthylmethyl group, a 2-naphthylmethyl group, a phenethyl group (a 2-phenylethyl group), a 1-phenylethyl group, a phenylpropyl group, a phenylbutyl group, a phenylpentyl group, a phenylhexyl group, a methylbenzyl group, a methylphenethyl group, a dimethylbenzyl group, a dimethylphenethyl group, a trimethylbenzyl group, an ethylbenzyl group and a diethylbenzyl group.

The arylalkenyl groups include a styryl group, a methylstyryl group, an ethylstyryl group, a dimethylstyryl group and a 3-phenyl-2-propenyl group.

The above hydrocarbon groups, in which the $CH_2$ group is substituted with a carbonyl group, a sulfonyl group, O or S, or the C—H group is substituted with N or C-halogen, include groups having one or more structures such as ketone, aldehyde, carboxylic acid, sulfone, ether, thioether, amine, alcohol, thiol, halogen and heterocycles (e.g. an oxygen-containing heterocycle, a sulfur-containing heterocycle, a nitrogen-containing heterocycle, etc.) The oxygen-containing heterocycle, sulfur-containing heterocycle and nitrogen-containing heterocycle correspond to cyclic hydrocarbon groups in which their ring carbon is substituted with oxygen, sulfur and nitrogen, respectively. These heterocycles may contain two or more heteroatoms.

These substituted hydrocarbon groups may include a ketone structure such as an acetylmethyl group and an acetylphenyl group; a sulfone structure such as a methanesulfonylmethyl group; an ether structure such as a methoxymethyl group, a methoxyethyl group, an ethoxyethyl group, a methoxypropyl group, a butoxyethyl group, an ethoxyethoxyethyl group, a methoxyphenyl group, dimethoxyphenyl group and phenoxymethyl group; a thioether structure such as a methylthiomethyl group and a methylthiophenyl group; an amine structure such as an aminomethyl group, a 2-aminoethyl group, a 2-aminopropyl group, a 3-aminopropyl group, a 2,3-diaminopropyl group, a 2-aminobutyl group, a 3-aminobutyl group, a 4-aminobutyl group, a 2,3-diaminobutyl group, a 2,4-diaminobutyl group, a 3,4-diaminobutyl group, a 2,3,4-triaminobutyl group, a methylaminomethyl group, a dimethylaminometyl group, a methylaminoethyl group, a propylaminomethyl group, a cyclopentylaminomethyl group, an aminophenyl group, a diaminophenyl group, an aminomethylphenyl group; an oxygen-containing heterocycle such as a tetrahydrofuranyl group, a tetrahydropyranyl group and a morphorylethyl group; an oxygen-containing aromatic ring such as a furyl group, a furfuryl group, a benzofuryl group and a benzofurfuryl group; a sulfur-containing heterocycle such as a thienyl group; a nitrogen-containing aromatic ring such as a pyrrolyl group, an imidazoyl group, an oxazoyl group, a thiadiazoyl group, a pyridyl group, a pyrimidyl group, a pyridazinyl group, a pyrazinyl group, a tetrazinyl group, a quinolyl group, an isoquinolyl group, a pyridylmethyl group; an alcohol structure such as a 2-hydroxyethyl group, a 2-hydroxypropyl group, a 3-hydroxypropyl group, a 2,3-dihydroxypropyl group, a 2-hydroxybutyl group, a 3-hydroxybutyl group, a 4-hydroxybutyl group, a 2,3-dihydroxybutyl group, a 2,4-dihydroxybutyl group, a 3,4-dihydroxybutyl group, a 2,3,4-trihydroxybutyl group, a hydroxyphenyl group, a dihydroxyphenyl group, a hydroxymethylphenyl group and a hydroxyethylphenyl group; a thiol structure such as a 2-mercaptoethyl group, a 2-mercaptopropyl group, a 3-mercaptopropyl group, a 2,3-dimercaptopropyl group, a 2-mercaptobutyl group, a 3-mercaptobutyl group, a 4-mercaptobutyl group, a mercaptophenyl group; a halogenated hydrocarbon group such as a 2-chloroethyl group, a 2-chloropropyl group, a 3-chloropropyl group, a 2-chlorobutyl group, a 3-chlorobutyl group, a 4-chlorobutyl group, a fluorophenyl group, a chlorophenyl group, a bromophenyl group, a difluorophenyl group, a dichlorophenyl group, a dibromophenyl group, a chlorofluorophenyl group, a trifluorophenyl group, a trichlorophenyl group, a fluoromethylphenyl group and a trifluoromethylpheyl group; a compound having both an amine structure and an alcohol structure such as a 2-amino-3-hydroxypropyl group, a 3-amino-2-hydroxypropyl group, a 2-amino-3-hydroxybutyl group, a 3-amino-2-hydroxybutyl group, a 2-amino-4-hydroxybutyl group, a 4-amino-2-hydroxybutyl group, a 3-amino-4-hydroxybutyl group, a 4-amino-3-hydroxybutyl group, a 2,4-diamino-3-hydroxybutyl group, a 3-amino-2,4-dihydroxybutyl group, a 2,3-diamino-4-hydroxybutyl group, a 4-amino-2,3-dihydroxybutyl group, a 3,4-diamino-2-hydroxybutyl group, a 2-amino-3,4-dihydroxybutyl group and an aminohydroxyphenyl group; a hydrocarbon group substituted with a halogen and a hydroxyl group such as a fluorohydroxyphenyl group, a chlorohydroxyphenyl group; and a carbon structure such as a carboxyphenyl group.

The cyanohydrin shown in the above formula (I) includes: 2-aryl-2-hydroxyacetonitrile such as mandelonitrile (2-hydroxy-2-phenylacetonitrile), 3-phenoxymandelonitrile (2-hydroxy-2-(3-phenoxyphenyl)acetonitrile), 4-methylmandelonitrile (2-hydroxy-2-(p-tolyl)acetonitrile), 2-chloromandelonitrile (2-(2-chlorophenyl)-2-hydroxyacetonitrile), 3-chloromandelonitrile (2-(3-chlorophenyl)-2-hydroxyacetonitrile), 4-chloromandelonitrile (2-(4-chlorophenyl)-2- hydroxyacetonitrile), 3-nitromandelonitrile (2-hydroxy-2-(3-nitrophenyl)acetonitrile), 3,4-methylenedioxymandelonitrile (2-hydroxy-2-(3,4-methylenedioxyphenyl) acetonitrile), 2,3-methylenedioxymandelonitrile (2-hydroxy-2-(2,3-methylenedioxyphenyl)acetonitrile), 2-benzyl-2-hydroxyacetonitrile and 2-(2-furyl)-2-hydroxyacetonitrile; 2-alkyl-2-hydroxyacetonitrile such as 2-hydroxy-2-methylacetonitrile, 2-hydroxy-2-propylacetonitrile, 2-hydroxy-2-isopropylacetonitrile, 2-butyl-2-hydroxyacetonitrile and 2-cyclohexyl-2-hydroxyacetonitrile; 2,2-dialkyl-2-hydroxyacetonitrile such as 2-ethyl-2-hydroxy-2-methylacetonitrile, 2-butyl-2-hydroxy-2-methylacetonitrile, 2-hydroxy-2-methyl-2-propylacetonitrile, 2-hydroxy-2-isopropyl-2-methylacetonitrile, 2-hydroxy-2-methyl-2-pentylacetonitrile, 2-hydroxy-2-methyl-2-(2-methylpropyl) acetonitrile and 2-hydroxy-2-methyl-2-(3-methylbutyl) acetonitrile; 2-alkyl-2-alkenyl-2-hydroxyacetonitrile such as 2-hydroxy-2-methyl-2-(2-propenyl)acetonitrile and 2-(3-butenyl)-2-hydroxy-2-methylacetonitrile; 2-alkyl-2-(haloalkyl)-2-hydroxyacetonitrile such as 2-(3-chloropropyl)-2-hydroxy-2-methylacetonitrile; 2-(1-(protected amino)alkyl)-2-hydroxyacetonitrile such as 2-(1-alkoxycarbonylamino)-2-cyclohexylethyl)-2-hydroxyacetonitrile; 2-alkylthioalkyl-2-hydroxyacetonitrile such as 2-hydroxy-2-(2-methylthioethyl)acetonitrile; and 2-acyl-2-hydroxyacetonitrile such as 2-hydroxy-2-pivaloilacetonitrile.

A divalent group represented by $R^1$ and $R^2$ is not particularly limited, and the examples include an alkylene group containing 2 to 22 carbon atoms, norbornane-2-ylidene and 2-norbornene-5-ylidene.

The cyanohydrin used for the first aspect of the present invention can be obtained by known methods, i.e. by allowing alkali cyanide to act on a corresponding carbonyl compound or its sodium hydrogensulfite adduct. In a case of the use of cyanohydrin of the above formula (I), wherein $R^1$ and $R^2$ are different from each other, any of a (S)-form and an (R) form can be used, and this compound can be produced by, for example, such methods as an optical resolution of cyanohydrin obtained by acting alkali cyanide with a corresponding carbonyl compound or its sodium hydrogensulfite adduct; a method of asymmetricly adding hydrogen cyanide to a corresponding carbonyl compound in the presence of enzymes such as (S)-hydroxynitrilelyase and (R)-hydroxynitrilelyase extracted from plants (e.g. *Synthesis*, July 1990, 575–578; *Tetrahedron Letters*, 32, 2605–2608 (1991); Japanese Patent Application Filed Nos. 63-219388, 5-317065 and 9-227488); a method of asymmetricly hydrolyzing a material obtained by chemical synthesis of racemic cyanohydrinester, using enzymes (e.g. Japanese Patent Application Filed No. 62-65688); and a method of asymmetricly adding hydrogen cyanide to a corresponding carbonyl compound in the presence of enzymes produced by a gene recombinant microorganism, into which a gene of enzymes such as (S)-hydroxynitrilelyase and (R)-hydroxynitrilelyase is incorporated (e.g. WO98/30711, Japanese Patent Application Filed No. 9-227488).

Mineral acid is preferably used for the hydrolysis in the first aspect of the present invention. The examples of such mineral acid include hydrochloric acid, sulfuric acid, nitric acid, boracic acid, phosphoric acid and perchloric acid, hydrochloric acid being preferable.

If an overfull usage of hydrolytic catalyst is used to cyanohydrin, it would be economically disadvantageous and lead to the decrease of the yield. However, the extremely low usage of catalyst would lead to a slow and insufficient reaction, or, in the use of optically active cyanohydrin as a material, it would lead to the reduction in the optical purity of the α-hydroxycarboxylic acid of interest. Accordingly, the preferable amount of hydrolytic catalyst is generally 1.5 to 10 equivalents to cyanohydrin, preferably 1.5 to 8 equivalents, and more preferably 2 to 7 equivalents.

Hereinafter, the hydrocarbon solvent used in the first aspect of the present invention is described. The hydrocarbon solvent used in the first aspect of the present invention is not particularly limited, as long as it is an organic compound consisting of carbon atoms and hydrogen atoms only, and it exists as a liquid at the reaction temperature of hydrolysis and separates from an aqueous phase.

Such carbon solvents include any of a linear or branched chain hydrocarbon, a cyclic hydrocarbon with or without side chain, and a chain hydrocarbon wherein the above cyclic hydrocarbon group is substituted. In addition, these hydrocarbons may have an unsaturated bond in a molecule thereof. Some representatives of the above hydrocarbon solvents are shown below.

The linear or branched chain hydrocarbon includes pentane, hexane, heptane, octane and these structural isomers, e.g. chain hydrocarbons containing 5 to 16 carbon atoms, such as 2-methylpentane and 3-methylpentane.

The cyclic hydrocarbon with or without side chain includes cyclopentane, cyclohexane and structural isomers thereof, e.g. saturated monocyclic hydrocarbons containing 6 to 16 carbon atoms, such as methylcyclopentane and methylcyclohexane, and aromatic hydrocarbons such as benzene, toluene, trimethylbenzene, o-xylene, m-xylene, p-xylene or an isomeric mixture of xylene.

Among these hydrocarbon solvents, benzene, toluene and p-xylene are preferable, and toluene is more preferable.

A mixed solvent consisting of the combination of at least two of the above hydrocarbon solvents may also be used.

In the production method of the first aspect of the present invention, the above cyanohydrin is hydrolyzed in the presence of the above hydrocarbon solvent. That is, the reaction is performed by adding a hydrocarbon solvent, water containing a hydrolytic catalyst and cyanohydrin as a material to a reaction vessel. When left at rest, the reaction solution divides into both a hydrocarbon solvent phase and an aqueous phase, so it is preferable to perform hydrolysis, while stirring the reaction solution appropriately.

The usage of a hydrocarbon solvent in the first aspect of the present invention is 10 to 200 weight % to cyanohydrin as a material, and preferably 20 to 100 weight %. The amount of water in the reaction mixture at initiation of the reaction is preferably 7 to 50 equivalents to cyanohydrin, and more preferably 10 to 40 equivalents.

In the production method of the first aspect of the present invention, when the maximum temperature at hydrolysis exceeds 90° C., the generation of by-products and coloration increases, or the purity of α-hydroxycarboxylic acid of interest is reduced. On the other hand, a reaction temperature of 40° C. or less leads to the reaction proceeding insufficiently, resulting in a decrease of the yield. Accordingly, the temperature of reaction solution at hydrolysis is preferably 40 to 90° C., and more preferably 50 to 80° C. In addition, the reaction time is preferably 1 to 24 hours, 2 to 12 hours being more preferable.

After completion of the reaction, the α-hydroxycarboxylic acid of interest is isolated from the reaction solution. If the reaction solution is left at rest after hydrolysis, it divides into both a hydrocarbon solvent phase containing colored substances and by-products, and an aqueous phase containing α-hydroxycarboxylic acid. So, at that moment, the hydrocarbon solvent phase is separated and removed from the reaction solution. Then, extraction is performed by adding an organic solvent such as ethyl acetate to the remaining aqueous phase, and if necessary, the organic phase is washed with water and the solvent removed from the organic phase, thereby obtaining high purity α-hydroxycarboxylic acid of interest.

In the production method of the first aspect of the present invention, impurities such as colored substances and by-products generated during hydrolysis are extracted from the aqueous phase to the hydrocarbon solvent phase, while the α-hydroxycarboxylic acid of interest remains in the aqueous phase, so that high purity α-hydroxycarboxylic acid can easily be obtained, while suppressing the coloration of the reaction solution (an aqueous phase) and α-hydroxycarboxylic acid.

The method of the second aspect of the present invention is to prevent reduction of the yield and optical purity of optically active α-hydroxycarboxylic acid caused by the use of an alcoholic solvent, an ester solvent, an ethereal solvent and/or a carboxylic solvent used in the production process of optically active cyanohydrin. The process of producing optically active cyanohydrin is not particularly limited, as long as these solvents are used as reaction solvents.

An example of the production process of optically active cyanohydrin includes a production process of optically active cyanohydrin by asymmetrically adding hydrogen cyanide to a carbonyl compound shown in the following formula (II):

$$R^1-CO-R^2 \qquad (II)$$

wherein $R^1$ and $R^2$ are different from each other, independently representing a hydrogen atom or a monovalent hydrocarbon group containing at most 22 carbon atoms, and in the above hydrocarbon group, each of —$CH_2$— and $CH_2$ in —$CH_3$ may be substituted with a carbonyl group, a sulfonyl group, —O— or —S—, =$CH_2$ may be substituted with =O or =S; or C—H in —$CH_2$, C—H in —$CH_3$, C—H in >CH—, C—H in =CH— and C—H in =$CH_2$ may be substituted with N or C-halogen, or $R^1$ and $R^2$ may together form an asymmetric divalent group, in the above organic solvent(s), in the presence of enzymes such as (S)-hydroxynitrilelyase and (R)-hydroxynitrilelyase extracted from plants or enzymes produced by a gene recombinant microorganism, into which a gene of those enzymes is incorporated (e.g. *Synthesis*, July 1990, 575–578; *Tetrahedron Letters*, 32, 2605–2608 (1991); Japanese Patent Application filed Nos. 63-219388, 5-317065 and 9-227488; WO98/30711).

The monovalent hydrocarbon group containing at most 22 carbon atoms in the above formula (II) includes a linear or branched chain hydrocarbon group, a monocyclic hydrocarbon group with or without side chain, a polycyclic hydrocarbon group with or without side chain, a spiro hydrocarbon group with or without side chain, a ring-assembled structural hydrocarbon group with or without side chain, or a chain hydrocarbon group with the above cyclic-hydrocarbon. It includes any saturated or unsaturated hydrocarbon group, with the exception of unsaturated hydrocarbon groups having an allene structure (C=C=C). The linear or branched chain hydrocarbon group includes, for example, saturated chain hydrocarbon groups such as a linear alkyl group containing at least 1 carbon atom and a branched alkyl group containing at least 3 carbon atoms; unsaturated chain hydrocarbon groups such as a linear alkenyl group containing at least 2 carbon atoms, a branched alkenyl group containing at least 3 carbon atoms, a linear alkynyl group containing at least 3 carbon atoms, a branched alkynyl group containing at least 4 carbon atoms, a linear alkadienyl group containing at least 4 carbon atoms and a branched alkadienyl group containing at least 5 carbon atoms. The monocyclic hydrocarbon group includes, for example, saturated monocyclic hydrocarbon groups such as a cycloalkyl group without side chain which contains at least 3 carbon atoms and a cycloalkyl group with side chain which contains at least 4 carbon atoms in total; unsaturated monocyclic hydrocarbon groups such as a cycloalkenyl group without side chain which contains at least 4 carbon atoms, a cycloalkynyl group with side chain which contains at least 5 carbon atoms in total, a cycloalkadienyl group without side chain which contains at least 5 carbon atoms and a cycloalkadienyl group with side chain which contains at least 6 carbon atoms in total. The unsaturated monocyclic or polycyclic hydrocarbon group includes an aromatic hydrocarbon group including: an aromatic group without side chain which contains 6 to 22 carbon atoms in total such as a phenyl group, a 1-naphthyl group, a 2-naphthyl group and a 9-anthryl group; an aromatic group with side chain which contains at least 7 carbon atoms in total; a phenylphenyl group containing 12 carbon atoms and a phenylphenyl group with side chain which contains at least 13 carbon atoms in total, which are also included in a ring-assembled structural hydrocarbon group. The polycyclic hydrocarbon group includes a condensed cyclic hydrocarbon group without side chain which contains at least 6 carbon atoms, a condensed cyclic hydrocarbon group with side chain which contains at least 7 carbon atoms in total, a bridged cyclic hydrocarbon group without side chain which contains at least 7 carbon atoms, a bridged cyclic hydrocarbon group with side chain which contains at least 8 carbon atoms in total, a spiro hydrocarbon group without side chain which contains at least 9 carbon atoms in total and a spiro hydrocarbon group with side chain which contains at least 10 carbon atoms in total. In addition, the above condensed cyclic hydrocarbon group without side chain includes those which contain at least 9 carbon atoms in total when one of its condensed rings is a benzene ring, and the above condensed cyclic hydrocarbon group with side chain includes those which contain at least 10 carbon atoms in total when one of its condensed rings is benzene ring. The ring-assembled structural hydrocarbon group includes a cycloalkyl-cycloalkyl group without side chain which contains at least 6 carbon atoms in total, a cycloalkyl-cycloalkyl group with side chain which contains at least 7 carbon atoms in total, a cycloalkylidene-cycloalkyl group with out side chain which contains at least 6 carbon atoms in total and a cycloalkylidene-cycloalkyl group with side chain which contains at least 7 carbon atoms in total. "A cyclic hydrocarbon with side chain" in these cyclic hydrocarbons, corresponds to one having a chain hydrocarbon group attached to its ring. The above chain hydrocarbon group having a cyclic hydrocarbon group includes a linear alkyl group which is substituted with an aromatic group without side chain and contains at least 7 carbon atoms in total, a linear alkyl group which is substituted with an aromatic group with side chain and contains at least 8 carbon atoms in total, a branched alkyl group which is substituted with an aromatic group without side chain and contains at least 9 carbon atoms in total, a branched alkyl group which is substituted with an aromatic group with side chain and contains at least 10 carbon atoms in total, a linear alkenyl group which is substituted with an aromatic group without side chain and contains at least 8 carbon atoms in total, a linear alkenyl group which is substituted with an aromatic group with side chain and contains at least 9 carbon atoms in total, a branched alkenyl group which is substituted with an aromatic group without side chain and contains at least 9 carbon atoms in total, a branched alkenyl group which is substituted with an aromatic group with side chain and contains at least 10 carbon atoms in total, a linear alkynyl group which is substituted with an aromatic group without side chain and contains at least 8 carbon atoms in total, a linear alkynyl group which is substituted with an aromatic group with side chain and contains at least 9 carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least 4 carbon atoms in total, a linear alkyl group which is substituted with a cycloalkyl group with side chain and contains at least 5 carbon atoms in total, a branched alkyl group which is substituted with a cycloalkyl group without side chain and contains at least 6 carbon atoms in total, a branched alkyl group which is substituted with a cycloalkyl group with side chain and contains at least 7 carbon atoms in total, a linear alkenyl group which is substituted with a cycloalkyl group without side chain and contains at least 5 carbon atoms in total, a linear alkenyl group which is substituted with a cycloalkyl group with side chain and contains at least 6 carbon atoms in total, a branched alkenyl group which is substituted with a cycloalkyl group without side chain and contains at least 6 carbon atoms in total, a branched alkenyl group which is substituted with a cycloalkyl group with side chain and contains at least 7 carbon atoms in total, a linear alkynyl group which is substituted with a cycloalkyl group without side chain and contains at least 5 carbon atoms in total, a linear alkynyl group which is substituted with a cycloalkyl group with side chain and contains at least 6 carbon atoms in total, a branched alkynyl group which is substituted with a cycloalkyl group without side chain and contains at least 7 carbon atoms in total, a branched alkynyl group which is substituted with a cycloalkyl group with side chain and contains at least 8 carbon atoms in total, a branched alkadienyl group which is substituted with a cycloalkyl group without side chain and contains at least 8 carbon atoms in total, a branched alkadienyl group which is substituted with a cycloalkyl group with side chain and contains at least 9 carbon atoms in total.

Hereinafter, each of an aromatic group without side chain, an aromatic group with side chain, and a phenylphenyl group or a phenylphenyl group with side chain, is referred as an aryl group, and a linear or branched alkyl group substituted with the aryl group or groups is referred as an aralkyl group. Other cyclic hydrocarbon groups referring to both one having side chains on its ring and one having no side chains, are simply referred as, for example, cycloalkyl groups, unless otherwise specified. Also, chain hydrocarbon groups referring to both linear one and branched one are simply referred as, for example, alkyl groups.

When —$CH_2$— in the above hydrocarbon group is substituted with a carbonyl group, sulfonyl group, —O— or —S—, a ketone, sulfone, ether or thioether structure is introduced therein, respectively. When —$CH_2$— in —$CH_3$ is substituted with a carbonyl group, —O— or —S—, it converts into a formyl (aldehyde) group, a hydroxyl group or a mercapto group, respectively. When a terminal =$CH_2$ is substituted with =O or =S, a ketone or thioketone structure is introduced therein. When C—H in —$CH_2$— is substituted with N, it converts into —NH—. When C—H in >CH— is substituted with N, it converts into >N—. When C—H in =CH— is substituted with N, it converts into =N—. When C—H in a terminal —$CH_3$ is substituted with N, —$NH_2$ is introduced therein. When C—H in =$CH_2$ is substituted with N, it converts into =NH. Further, each C—H in —$CH_3$, —$CH_2$—, =CH—, ≡CH or >CH— is substituted with a C-halogen, the carbon is substituted with a halogen atom. The substitution of carbon chains with —O—, —S— or N corresponds to oxa-, thia- or aza-substitution of the hydrocarbon group, respectively. For example, when these substitution take place in a ring carbon of the hydrocarbon ring, the hydrocarbon ring converts into a heterocyclic ring respectively containing oxygen, sulfur or nitrogen. The substitution of $CH_2$ and C—H in the hydrocarbon group may independently take place and it may further take place when $CH_2$ or C—H still remains on the carbon after the prior substitution. Further, the above substitutions may bring the conversion of —$CH_2$—$CH_3$ into —CO—O—H, a carboxylic acid structure.

A halogen atom, herein, refers to a fluorine atom, a chlorine atom, a bromine atom and an iodine atom, but a fluorine atom, a chlorine atom and a bromine atom are preferable.

Accordingly, the above hydrocarbon group may be selected from any chain hydrocarbon group and hydrocarbon group having ring-structured hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include a methyl group, an ethyl group, a propyl group, an isopropyl group, a butyl group, a 1-methylpropyl group, a pentyl group, a 1-methylbutyl group, a hexyl group, a 1-methylpentyl group, a heptyl group, a 1-methylhexyl group, a 1-ethylpentyl group, an octyl group, a nonyl group, a decyl group, an undecyl group, a dodecyl group, a tridecyl group, a tetradecyl group, a 2-methylpropyl group, a 2-methylbutyl group, a 3-methylbutyl group, a 2-methylpentyl group, a 3-methylpentyl group, a 4-methylpentyl group, a methylhexyl group, a methylheptyl group, a methyloctyl group, a methylnonyl group, a 1,1-dimethylethyl group, a 1,1-dimethylpropyl group, a 2,6-dimethylheptyl group, a 3,7-dimethyloctyl group and a 2-ethylhexyl group; cycloalkylalkyl groups include a cyclopentylmethyl group and a cyclohexylmethyl group; cycloalkyl groups include a cyclopropyl group, a cyclobutyl group, a cyclopentyl group, a methylcyclopentyl group, a cyclohexyl group, a methylcyclohexyl group, a cycloheptyl group and a cyclooctyl group; and bicycloalkyl groups include a norbornyl group, a bicyclo [2.2.2] octyl group and an adamantyl group.

The linear or branched alkenyl groups include a vinyl group, an allyl group, a crotyl group (a 2-butenyl group) and an isopropenyl group (a 1-methylvinyl group); cycloalkenyl or cycloalkadienyl groups include a cyclopentenyl group, a cyclopentadienyl group, a cyclohexenyl group and a cyclohexadienyl group.

The linear or branched alkynyl groups include an ethynyl group, a propynyl group and a butynyl group. The aryl groups include a phenyl group, a 1-naphthyl group, a 2-naphthyl group, a 2-phenylphenyl group, a 3-phenylphenyl group, a 4-phenylphenyl group, a 9-anthryl group, a methylphenyl group, a dimethylphenyl group, a trimethylphenyl group, an ethylphenyl group, a methylethylphenyl group, a diethylphenyl group, a propylphenyl group and a butylphenyl group.

The aralkyl groups include a benzyl group, a 1-naphthylmethyl group, a 2-naphthylmethyl group, a phenethyl group (a 2-phenylethyl group), a 1-phenylethyl group, a phenylpropyl group, a phenylbutyl group, a phenylpentyl group, a phenylhexyl group, a methylbenzyl group, a methylphenethyl group, a dimethylbenzyl group, a dimethylphenethyl group, a trimethylbenzyl group, an ethylbenzyl group and a diethylbenzyl group.

The arylalkenyl groups include a styryl group, a methylstyryl group, an ethylstyryl group, a dimethylstyryl group and a 3-phenyl-2-propenyl group.

The above hydrocarbon groups, in which the $CH_2$ group is substituted with a carbonyl group, a sulfonyl group, O or S, or the C—H group is substituted with N or C-halogen, include groups having one or more structures such as ketone, aldehyde, carboxylic acid, sulfone, ether, thioether, amine, alcohol, thiol, halogen and heterocycles (e.g. an oxygen-containing heterocycle, a sulfur-containing heterocycle, a nitrogen-containing heterocycle, etc.) The oxygen-containing heterocycle, sulfur-containing heterocycle and nitrogen-containing heterocycle correspond to cyclic hydrocarbon groups in which their ring carbon is substituted with oxygen, sulfur and nitrogen, respectively. These heterocycles may contain two or more heteroatoms.

These substituted hydrocarbon groups may include a ketone structure such as an acetylmethyl group and an acetylphenyl group; a sulfone structure such as a methanesulfonylmethyl group; an ether structure such as a methoxymethyl group, a methoxyethyl group, an ethoxyethyl group, a methoxypropyl group, a butoxyethyl group, an ethoxyethoxyethyl group, a methoxyphenyl group, dimethoxyphenyl group and phenoxymethyl group; a thioether structure such as a methylthiomethyl group and a methylthiophenyl group; an amine structure such as an aminomethyl group, a 2-aminoethyl group, a 2-aminopropyl group, a 3-aminopropyl group, a 2,3-diaminopropyl group, a 2-aminobutyl group, a 3-aminobutyl group, a 4-aminobutyl group, a 2,3-diaminobutyl group, a 2,4-diaminobutyl group, a 3,4-diaminobutyl group, a 2,3,4-triaminobutyl group, a methylaminomethyl group, a dimethylaminometyl group, a methylaminoethyl group, a propylaminomethyl group, a cyclopentylaminomethyl group, an aminophenyl group, a diaminophenyl group, an aminomethylphenyl group; an oxygen-containing heterocycle such as a tetrahydrofuranyl group, a tetrahydropyranyl group and a morphorylethyl group; an oxygen-containing aromatic ring such as a furyl group, a furfuryl group, a benzofuryl group and a benzofurfuryl group; a sulfur-containing heterocycle such as a thienyl group; a nitrogen-containing aromatic ring such as a pyrrolyl group, an imidazoyl group, an oxazoyl group, a thiadiazoyl group, a pyridyl group, a pyrimidyl group, a pyridazinyl group, a pyrazinyl group, a tetrazinyl group, a quinolyl group, an isoquinolyl group, a pyridylmethyl group; an alcohol structure such as a 2-hydroxyethyl group, a 2-hydroxypropyl group, a 3-hydroxypropyl group, a 2,3-dihydroxypropyl group, a 2-hydroxybutyl group, a 3-hydroxybutyl group, a 4-hydroxybutyl group, a 2,3-dihydroxybutyl group, a 2,4-dihydroxybutyl group, a 3,4-dihydroxybutyl group, a 2,3,4-trihydroxybutyl group, a hydroxyphenyl group, a dihydroxyphenyl group, a hydroxymethylphenyl group and a hydroxyethylphenyl group; a thiol structure such as a 2-mercaptoethyl group, a 2-mercaptopropyl group, a 3-mercaptopropyl group, a 2,3-dimercaptopropyl group, a 2-mercaptobutyl group, a 3-mercaptobutyl group, a 4-mercaptobutyl group, a mercaptophenyl group; a halogenated hydrocarbon group such as a 2-chloroethyl group, a 2-chloropropyl group, a 3-chloropropyl group, a 2-chlorobutyl group, a 3-chlorobutyl group, a 4-chlorobutyl group, a fluorophenyl group, a chlorophenyl group, a bromophenyl group, a difluorophenyl group, a dichlorophenyl group, a dibromophenyl group, a chlorofluorophenyl group, a trifluorophenyl group, a trichlorophenyl group, a fluoromethylphenyl group and a trifluoromethylpheyl group; a compound having both an amine structure and an alcohol structure such as a 2-amino-3-hydroxypropyl group, a 3-amino-2-hydroxypropyl group, a 2-amino-3-hydroxybutyl group, a 3-amino-2-hydroxybutyl group, a 2-amino-4-hydroxybutyl group, a 4-amino-2-hydroxybutyl group, a 3-amino-4-hydroxybutyl group, a 4-amino-3-hydroxybutyl group, a 2,4-diamino-3-hydroxybutyl group, a 3-amino-2,4-dihydroxybutyl group, a 2,3-diamino-4-hydroxybutyl group, a 4-amino-2,3-dihydroxybutyl group, a 3,4-diamino-2-hydroxybutyl group, a 2-amino-3,4-dihydroxybutyl group and an aminohydroxyphenyl group; a hydrocarbon group substituted with a halogen and a hydroxyl group such as a fluorohydroxyphenyl group, a chlorohydroxyphenyl group; and a carbon structure such as a carboxyphenyl group.

An asymmetric divalent group represented by $R^1$ and $R^2$ is not particularly limited, and the examples include norbornane-2-ylidene and 2-norbornene-5-ylidene.

The carbonyl compound shown in the above formula (II) includes: aromatic aldehyde such as benzaldehyde, m-phenoxybenzaldehyde, p-methylbenzaldehyde, o-chlorobenzaldehyde, m-chlorobenzaldehyde, p-chlorobenzaldehyde, m-nitrobenzaldehyde, 3,4-methylenedioxybenzaldehyde, 2,3-methylenedioxybenzaldehyde, phenylacetoaldehyde and furfural; aliphatic aldehyde such as acetoaldehyde, butylaldehyde, isobutylaldehyde, valeraldehyde and cyclohexanealdehyde; saturated aliphatic ketone such as ethylmethylketone, butylmethylketone, methylpropylketone, isopropylmethylketone, methylpentylketone, methyl(2-methylpropyl)ketone and methyl(3-methylbutyl)keton; unsaturated aliphatic ketone such as methyl(2-propenyl)ketone and (3-butenyl)methylketone; alkyl(haloalkyl)ketone such as (3-chloropropyl)methylketone; 2-(protected amino) aldehyde such as 2-(alkoxycarbonylamino)-3-cyclohexylpropionealdehyde; and alkylthio aliphatic aldehyde such as 3-methylthiopropionealdehyde.

In the production process of optically active cyanohydrin in the method of the second aspect of the present invention, a solvent comprising at least one organic solvent selected from a group consisting of an alcoholic solvent, an ester solvent, an ethereal solvent and a carboxylic solvent is used as a reaction solvent.

The alcoholic solvent includes aliphatic alcohol such as methanol, ethanol, propanol, isopropanol, 1-butanol, 2-butanol, isobutanol, t-butanol, hexanol, n-amylalcohol and cyclohexanol as well as benzylalcohol and so on.

The ester solvent includes aliphatic ester such as methyl formate, methyl acetate, ethyl acetate, butyl acetate and methyl propionate.

The ethereal solvent includes aliphatic ether such as diethyl ether, dipropyl ether, diisopropyl ether, dibutyl ether, t-butylmethyl ether, dimethoxyethane and tetrahydrofuran.

The carboxylic solvent includes aliphatic carboxylic acid such as acetic acid.

Apart from the solvents listed above, the reaction solvent used in the second aspect of the present invention may also comprise a hydrocarbon-based solvent such as n-pentane, n-hexane, cyclohexane, benzene, toluene and xylene, and an aqueous buffer of pH 7 or less such as a citrate buffer, a phosphate buffer and an acetate buffer.

In the production process of optically active cyanohydrin in the method of the second aspect of the present invention, the use of the carbonyl compound of the above formula (II) as a material results in the generation of optically active cyanohydrin corresponding to the above compound shown in the following formula (III):

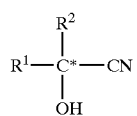

(III)

wherein $R^1$ and $R^2$ have the same definitions as $R^1$ and $R^2$ in the above formula (II), and C* represents an asymmetric carbon atom. Subsequent to that, in the method of the second aspect of the present invention, the as-is optically active cyanohydrin obtained in the first step, without isolation, is used for hydrolysis of the second step.

In the method of the second aspect of the present invention, an alcoholic solvent, an ester solvent, an ethereal solvent and/or a carboxylic solvent used as a reaction solvent in the first step were removed at that stage. Where a hydrocarbon-based solvent such as n-pentane, n-hexane, cyclohexane, benzene, toluene and xylene is used in combination with these organic solvent, the hydrocarbon-based solvent may not be removed.

Methods for removing the above solvent include, evaporation under an ordinary or reduced pressure, extraction with water and so on, but among these methods, evaporation under a reduced pressure is preferable in that this method is simple, having less influence on the second step.

Preferably, the removal of a reaction solvent in the first step of the second aspect of the present invention is preferably performed so that the amount of an alcoholic solvent, an ester solvent, an ethereal solvent and a carboxylic solvent in a reaction mixture subjected to hydrolysis is less than 10 weight %, and more preferably 5 weight %.

It is preferable to use mineral acid in performing hydrolysis in the second step of the second aspect of the present invention. Examples of mineral acid used herein include hydrochloric acid, sulfuric acid, nitric acid, boracic acid, phosphoric acid and perchloric acid, being hydrochloric acid preferable.

The preferable usage of mineral acid is 1 to 10 equivalents to optically active cyanohydrin which is contained in a reaction mixture subjected to hydrolysis. The usage of mineral acid of more than 10 equivalents to optically active cyanohydrin would be economically disadvantageous, resulting in the decrease of yield. However, the usage of mineral acid of less than 1 equivalent to optically active cyanohydrin would lead to a slow and insufficient reaction, or the reduction in the optical purity of optically active α-hydroxycarboxylic acid of interest. The more preferable usage of mineral acid is 2 to 8 equivalents to optically active cyanohydrin.

Preferably, hydrolysis is performed under the condition of the maximum reaction temperature of 40 to 90° C. The maximum reaction temperature of more than 90° C. would bring on the increase of by-products and coloration. On the other hand, the maximum reaction temperature of less than 40° C. would result in the insufficient proceeding of reaction. Furthermore, in both cases, the optical purity of optically active α-hydroxycarboxylic acid of interest is reduced. The maximum reaction temperature is more preferably 40 to 80° C. Where the reaction temperature is less than 40° C., the reaction time is preferably set at 15 hours or less, more preferably 3 hours or less.

In hydrolysis reaction, a reaction solvent may be used, but such a solvent is not only particularly effective but may also reduce yield or optical purity, so it is preferable not to use solvents other than water. At the initiation of reaction, the amount of water contained in a reaction mixture including water contained in mineral acid used, is preferably 7 to 50 equivalents to optically active cyanohydrin, and more preferably 10 to 40 equivalents.

After reaction, to isolate α-hydroxycarboxylic acid of interest from the obtained reaction solution (which, at times, may become, a slurry), the solution is extracted with an organic solvent and is washed, as needed, and then the solvent is vaporized and exsiccated.

As stated above, by converting the cyano group of optically active cyanohydrin into a carboxyl group, while maintaining the configuration of the above optically active cyanohydrin, α-hydroxycarboxylic acid can be produced.

The method of the third aspect of the present invention is a method for producing optically active α-hydroxycarboxylic acid by conversion of the cyano group of optically active cyanohydrin used as a material into a carboxyl group, while maintaining the configuration of the above optically active cyanohydrin, and according to the present method, it becomes possible to selectively produce optical isomers depending on the selection of (S)-form or (R)-form of cyanohydrin as a material.

The optically active cyanohydrin used as a material in the third aspect of the present invention is not particularly limited, as long as the cyanohydrin is an optically active substance (optically active α-hydroxynitrile) having, in a molecule thereof, at least one pair consisting of a hydroxyl group and a cyano group binding to an identical carbon atom. The optical purity of the above cyanohydrin is not particularly limited, as long as the purity is more than 80%, but an optical purity of 90 to 100% is preferable.

An example of optically active cyanohydrin used in the third aspect of the present invention includes a compound shown in the following formula (IV):

(IV)

wherein
C* is an asymmetric carbon atom;
$R^1$ and $R^2$ are different from each other, independently representing a hydrogen atom, a halogen atom, an amino group, an amino group mono- or di-substituted with a monovalent hydrocarbon group containing at most 14 carbon atoms, a mercapto group or a monovalent hydrocarbon group containing at most 22 carbon atoms, in the above hydrocarbon group, each of —$CH_2$— and $CH_2$ in —$CH_3$ may be substituted with a carbonyl group, sulfonyl group, —O— or —S—, =$CH_2$ may be substituted with =O or =S; or C—H in —$CH_2$, C—H in —$CH_3$, C—H in >CH—, C—H in =CH— and C—H in =$CH_2$ may be substituted with N or C-halogen, or $R^1$ and $R^2$ may together form an asymmetric divalent group.

The monovalent hydrocarbon group containing at most 22 carbon atoms in the above formula (IV) includes a linear or branched chain hydrocarbon group, a monocyclic hydrocarbon group with or without side chain, a polycyclic hydrocarbon group with or without side chain, a spiro hydrocarbon group with or without side chain, a ring-assembled structural hydrocarbon group with or without side chain, or a chain hydrocarbon group with the above cyclic-hydrocarbon. It includes any saturated or unsaturated hydrocarbon group, with the exception of unsaturated hydrocarbon groups having an allene structure (C=C=C). The linear or branched chain hydrocarbon group includes, for example, saturated chain hydrocarbon groups such as a linear alkyl group containing at least 1 carbon atom and a branched alkyl group containing at least 3 carbon atoms; unsaturated chain hydrocarbon groups such as a linear alkenyl group containing at least 2 carbon atoms, a branched alkenyl group containing at least 3 carbon atoms, a linear alkynyl group containing at least 3 carbon atoms, a branched alkynyl group containing at least 4 carbon atoms, a linear alkadienyl group containing at least 4 carbon atoms and a branched alkadienyl group containing at least 5 carbon atoms. The monocyclic hydrocarbon group includes, for example, saturated monocyclic hydrocarbon groups such as a cycloalkyl group without side chain which contains at least 3 carbon atoms and a cycloalkyl group with side chain which contains at least 4 carbon atoms in total; unsaturated monocyclic hydrocarbon groups such as a cycloalkenyl group without side chain which contains at least 4 carbon atoms, a cycloalkynyl group with side chain which contains at least 5 carbon atoms in total, a cycloalkadienyl group without side chain which contains at least 5 carbon atoms and a cycloalkadienyl group with side chain which contains at least 6 carbon atoms in total. The unsaturated monocyclic or polycyclic hydrocarbon group includes an aromatic hydrocarbon group including: an aromatic group without side chain which contains 6 to 22 carbon atoms in total such as a phenyl group, a 1-naphthyl group, a 2-naphthyl group and a 9-anthryl group; an aromatic group with side chain which contains at least 7 carbon atoms in total; a phenylphenyl group containing 12 carbon atoms and a phenylphenyl group with side chain which contains at least 13 carbon atoms in total, which are also included in a ring-assembled structural hydrocarbon group. The polycyclic hydrocarbon group includes a condensed cyclic hydrocarbon group without side chain which contains at least 6 carbon atoms, a condensed cyclic hydrocarbon group with side chain which contains at least 7 carbon atoms in total, a bridged cyclic hydrocarbon group with out side chain which contains at least 7 carbon atoms, a bridged cyclic hydrocarbon group with side chain which contains at least 8 carbon atoms in total, a spirohydrocarbon group without side chain which contains at least 9 carbon atoms in total and a spiro hydrocarbon group with side chain which contains at least 10 carbon atoms in total. In addition, the above condensed cyclic hydrocarbon group without side chain includes those which contain at least 9 carbon atoms in total when one of its condensed rings is a benzene ring, and the above condensed cyclic hydrocarbon group with side chain includes those which contain at least 10 carbon atoms in total when one of its condensed rings is benzene ring. The ring-assembled structural hydrocarbon group includes a cycloalkyl-cycloalkyl group without side chain which contains at least 6 carbon atoms in total, a cycloalkyl-cycloalkyl group with side chain which contains at least 7 carbon atoms in total, a cycloalkylidene-cycloalkyl group without side chain which contains at least 6 carbon atoms in total and a cycloalkylidene-cycloalkyl group with side chain which contains at least 7 carbon atoms in total. "A cyclic hydrocarbon with side chain" in these cyclic hydrocarbons, corresponds to one having a chain hydrocarbon group attached to its ring. Such chain hydrocarbon group having a cyclic hydrocarbon group includes a linear alkyl group which is substituted with an aromatic group without side chain and contains at least 7 carbon atoms in total, a linear alkyl group which is substituted with an aromatic group with side chain and contains at least 8 carbon atoms in total, a branched alkyl group which is substituted with an aromatic group without side chain and contains at least 9 carbon atoms in total, a branched alkyl group which is substituted with an aromatic group with side chain and contains at least 10 carbon atoms in total, a linear alkenyl group which is substituted with an aromatic group without side chain and contains at least 8 carbon atoms in total, a linear alkenyl group which is substituted with an aromatic group with side chain and contains at least 9 carbon atoms in total, a branched alkenyl group which is substituted with an aromatic group without side chain and contains at least 9 carbon atoms in total, a branched alkenyl group which is substituted with an aromatic group with side chain and contains at least 10 carbon atoms in total, a linear alkynyl group which is substituted with an aromatic group without side chain and contains at least 8 carbon atoms in total, a linear alkynyl group which is substituted with an aromatic group with side chain and contains at least 9 carbon atoms in total, a branched alkynyl group which is substituted with an aromatic group without side chain and contains at least 10 carbon atoms in total, a branched alkynyl group which is substituted with an aromatic group with side chain and contains at least 11 carbon atoms in total, a linear alkadienyl group which is substituted with an aromatic group without side chain and contains at least 10 carbon atoms in total, a linear alkadienyl group which is substituted with an aromatic group with side chain and contains at least 11 carbon atoms in total, a branched alkadienyl group which is substituted with an aromatic group without side chain and contains at least 11 carbon atoms in total, a branched alkadienyl group which is substituted with an aromatic group with side chain and contains at least 12 carbon atoms in total, a linear alkyl group which is substituted with a cycloalkyl group without side chain and contains at least 4 carbon atoms in total, a linear alkyl group which is substituted with a cycloalkyl group with side chain and contains at least 5 carbon atoms in total, a branched alkyl group which is substituted with a cycloalkyl group without side chain and contains at least 6 carbon atoms in total, a branched alkyl group which is substituted with a cycloalkyl group with side chain and contains at least 7 carbon atoms in total, a linear alkenyl group which is substituted with a cycloalkyl group without side chain and contains at least 5 carbon atoms in total, a linear alkenyl group which is substituted with a cycloalkyl group with side chain and contains at least 6 carbon atoms in total, a branched alkenyl group which is substituted with a cycloalkyl group without side chain and contains at least 6 carbon atoms in total, a branched alkenyl group which is substituted with a cycloalkyl group with side chain and contains at least 7 carbon atoms in total, a linear alkynyl group which is substituted with a cycloalkyl group without side chain and contains at least 5 carbon atoms in total, a linear alkynyl group which is substituted with a cycloalkyl group with side chain and contains at least 6 carbon atoms in total, a branched alkynyl group which is substituted with a cycloalkyl group without side chain and contains at least 7 carbon atoms in total, a branched alkynyl group which is substituted with a cycloalkyl group with side chain and contains at least 8 carbon atoms in total, a branched alkadienyl group which is substituted with a cycloalkyl group without side chain and contains at least 8 carbon atoms in total, a branched alkadienyl group which is substituted with a cycloalkyl group with side chain and contains at least 9 carbon atoms in total.

Hereinafter, each of an aromatic group without side chain, an aromatic group with side chain, and a phenylphenyl group or a phenylphenyl group with side chain, is referred as an aryl group, and a linear or branched alkyl group substituted with the aryl group or groups is referred as an aralkyl group. Other cyclic hydrocarbon groups referring to both one having side chains on its ring and one having no side chains, are simply referred as, for example, cycloalkyl groups, unless otherwise specified. Also, chain hydrocarbon groups referring to both linear one and branched one are simply referred as, for example, alkyl groups.

When —$CH_2$— in the above hydrocarbon group is substituted with a carbonyl group, sulfonyl group, —O— or —S—, a ketone, sulfone, ether or thioether structure is introduced therein, respectively. When —$CH_2$— in —$CH_3$ is substituted with a carbonyl group, —O— or —S—, it converts into a formyl (aldehyde) group, a hydroxyl group or a mercapto group, respectively. When a terminal =$CH_2$ is substituted with =O or =S, a ketone or thioketone structure is introduced therein. When C—H in —$CH_2$— is substituted with N, it converts into —NH—. When C—H in >CH— is substituted with N, it converts into >N—. When C—H in =CH— is substituted with N, it converts into =N—. When C—H in a terminal —$CH_3$ is substituted with N, —$NH_2$ is introduced therein. When C—H in =$CH_2$ is substituted with N, it converts into =NH. Further, each C—H in —$CH_3$, —$CH_2$—, =CH—, ≡CH or >CH— is substituted with a C-halogen, the carbon is substituted with a halogen atom. The substitution of carbon chains with —O—, —S— or N corresponds to oxa-, thia- or aza-substitution of the hydrocarbon group, respectively. For example, when these substitution take place in a ring carbon of the hydrocarbon ring, the hydrocarbon ring converts into a heterocyclic ring respectively containing oxygen, sulfur or nitrogen. The substitution of $CH_2$ and C—H in the hydrocarbon group may independently take place and it may further take place when $CH_2$ or C—H still remains on the carbon after the prior substitution. Further, the above substitutions may bring the conversion of —$CH_2$—$CH_3$ into —CO—O—H, a carboxylic acid structure.

A halogen atom, herein, refers to a fluorine atom, a chlorine atom, a bromine atom and an iodine atom, but a fluorine atom, a chlorine atom and a bromine atom are preferable.

Accordingly, the above hydrocarbon group may be selected from any chain hydrocarbon group and hydrocarbon group having ring-structured hydrocarbon group such as cyclic hydrocarbon groups, for example, saturated chain hydrocarbon groups such as linear or branched alkyl groups; unsaturated chain hydrocarbon groups such as linear or branched alkenyl groups, linear or branched alkynyl groups and linear or branched alkadienyl groups; saturated cyclic hydrocarbon groups such as cycloalkyl groups; unsaturated cyclic hydrocarbon groups such as cycloalkenyl groups, cycloalkynyl groups and cycloalkadienyl groups; and aromatic hydrocarbon groups such as aryl groups, aralkyl groups and arylalkenyl groups.

In more detail, the linear or branched alkyl groups include a methyl group, an ethyl group, a propyl group, an isopropyl group, a butyl group, a 1-methylpropyl group, a pentyl group, a 1-methylbutyl group, a hexyl group, a 1-methylpentyl group, a heptyl group, a 1-methylhexyl group, a 1-ethylpentyl group, an octyl group, a nonyl group, a decyl group, an undecyl group, a dodecyl group, a tridecyl group, a tetradecyl group, a 2-methylpropyl group, a 2-methylbutyl group, a 3-methylbutyl group, a 2-methylpentyl group, a 3-methylpentyl group, a 4-methylpentyl group, a methylhexyl group, a methylheptyl group, a methyloctyl group, a methylnonyl group, a 1,1-dimethylethyl group, a 1,1-dimethylpropyl group, a 2,6-dimethylheptyl group, a 3,7-dimethyloctyl group and a 2-ethylhexyl group; cycloalkylalkyl groups include a cyclopentylmethyl group and a cyclohexylmethyl group; cycloalkyl groups include a cyclopropyl group, a cyclobutyl group, a cyclopentyl group, a methylcyclopentyl group, a cyclohexyl group, a methylcyclohexyl group, a cycloheptyl group and a cyclooctyl group; and bicycloalkyl groups include a norbornyl group, a bicyclo [2.2.2] octyl group and an adamantyl group.

The linear or branched alkenyl groups include a vinyl group, an allyl group, a crotyl group (a 2-butenyl group) and an isopropenyl group (a 1-methylvinyl group); cycloalkenyl or cycloalkadienyl groups include a cyclopentenyl group, a cyclopentadienyl group, a cyclohexenyl group and a cyclohexadienyl group.

The linear or branched alkynyl groups include an ethynyl group, a propynyl group and a butynyl group. The aryl groups include a phenyl group, a 1-naphthyl group, a 2-naphthyl group, a 2-phenylphenyl group, a 3-phenylphenyl group, a 4-phenylphenyl group, a 9-anthryl group, a methylphenyl group, a dimethylphenyl group, a trimethylphenyl group, an ethylphenyl group, a methylethylphenyl group, a diethylphenyl group, a propylphenyl group and a butylphenyl group.

The aralkyl groups include a benzyl group, a 1-naphthylmethyl group, a 2-naphthylmethyl group, a phenethyl group (a 2-phenylethyl group), a 1-phenylethyl group, a phenylpropyl group, a phenylbutyl group, a phenylpentyl group, a phenylhexyl group, a methylbenzyl group, a methylphenethyl group, a dimethylbenzyl group, a dimethylphenethyl group, a trimethylbenzyl group, an ethylbenzyl group and a diethylbenzyl group.

The arylalkenyl groups include a styryl group, a methylstyryl group, an ethylstyryl group, a dimethylstyryl group and a 3-phenyl-2-propenyl group.

The above hydrocarbon groups, in which the $CH_2$ group is substituted with a carbonyl group, a sulfonyl group, O or S, or the C—H group is substituted with N or C-halogen, include groups having one or more structures such as ketone, aldehyde, carboxylic acid, sulfone, ether, thioether, amine, alcohol, thiol, halogen and heterocycles (e.g. an oxygen-containing heterocycle, a sulfur-containing heterocycle, a nitrogen-containing heterocycle etc.) The oxygen-containing heterocycle, sulfur-containing heterocycle and nitrogen-containing heterocycle correspond to cyclic hydrocarbon groups in which their ring carbon is substituted with oxygen, sulfur and nitrogen, respectively. These heterocycles may contain two or more heteroatoms.

These substituted hydrocarbon groups may include a ketone structure such as an acetylmethyl group and an acetylphenyl group; a sulfone structure such as a methanesulfonylmethyl group; an ether structure such as a methoxymethyl group, a methoxyethyl group, an ethoxyethyl group, a methoxypropyl group, a butoxyethyl group, an ethoxyethoxyethyl group, a methoxyphenyl group, dimethoxyphenyl group and phenoxymethyl group; a thio-ether structure such as a methylthiomethyl group and a methylthiophenyl group; an amine structure such as an aminomethyl group, a 2-aminoethyl group, a 2-aminopropyl group, a 3-aminopropyl group, a 2,3-diaminopropyl group, a 2-aminobutyl group, a 3-aminobutyl group, a 4-aminobutyl group, a 2,3-diaminobutyl group, a 2,4-diaminobutyl group, a 3,4-diaminobutyl group, a 2,3,4-triaminobutyl group, a methylaminomethyl group, a dimethylaminometyl group, a methylaminoethyl group, a propylaminomethyl group, a cyclopentylaminomethyl group, an aminophenyl group, a diaminophenyl group, an aminomethylphenyl group; an oxygen-containing heterocycle such as a tetrahydrofuranyl group, a tetrahydropyranyl group and a morphorylethyl group; an oxygen-containing aromatic ring such as a furyl group, a furfuryl group, a benzofuryl group and a benzofurfuryl group; a sulfur-containing heterocycle such as a thienyl group; a nitrogen-containing aromatic ring such as a pyrrolyl group, an imidazoyl group, an oxazoyl group, a thiadiazoyl group, a pyridyl group, a pyrimidyl group, a pyridazinyl group, a pyrazinyl group, a tetrazinyl group, a quinolyl group, an isoquinolyl group, a pyridylmethyl group; an alcohol structure such as a 2-hydroxyethyl group, a 2-hydroxypropyl group, a 3-hydroxypropyl group, a 2,3-dihydroxypropyl group, a 2-hydroxybutyl group, a 3-hydroxybutyl group, a 4-hydroxybutyl group, a 2,3-dihydroxybutyl group, a 2,4-dihydroxybutyl group, a 3,4-dihydroxybutyl group, a 2,3,4-trihydroxybutyl group, a hydroxyphenyl group, a dihydroxyphenyl group, a hydroxymethylphenyl group and a hydroxyethylphenyl group; a thiol structure such as a 2-mercaptoethyl group, a 2-mercaptopropyl group, a 3-mercaptopropyl group, a 2,3-dimercaptopropyl group, a 2-mercaptobutyl group, a 3-mercaptobutyl group, a 4-mercaptobutyl group, a mercaptophenyl group; a halogenated hydrocarbon group such as a 2-chloroethyl group, a 2-chloropropyl group, a 3-chloropropyl group, a 2-chlorobutyl group, a 3-chlorobutyl group, a 4-chlorobutyl group, a fluorophenyl group, a chlorophenyl group, a bromophenyl group, a difluorophenyl group, a dichlorophenyl group, a dibromophenyl group, a chlorofluorophenyl group, a trifluorophenyl group, a trichlorophenyl group, a fluoromethylphenyl group and a trifluoromethylpheyl group; a compound having both an amine structure and an alcohol structure such as a 2-amino-3-hydroxypropyl group, a 3-amino-2-hydroxypropyl group, a 2-amino-3-hydroxybutyl group, a 3-amino-2-hydroxybutyl group, a 2-amino-4-hydroxybutyl group, a 4-amino-2-hydroxybutyl group, a 3-amino-4-hydroxybutyl group, a 4-amino-3-hydroxybutyl group, a 2,4-diamino-3-hydroxybutyl group, a 3-amino-2,4-dihydroxybutyl group, a 2,3-diamino-4-hydroxybutyl group, a 4-amino-2,3-dihydroxybutyl group, a 3,4-diamino-2-hydroxybutyl group, a 2-amino-3,4-dihydroxybutyl group and an aminohydroxyphenyl group; a hydrocarbon group substituted with a halogen and a hydroxyl group such as a fluorohydroxyphenyl group, a chlorohydroxyphenyl group; and a carbon structure such as a carboxyphenyl group.

The cyanohydrin shown in the above formula (IV) includes: 2-aryl-2-hydroxyacetonitrile such as mandelonitrile (2-hydroxy-2-phenylacetonitrile), 3-phenoxymandelonitrile (2-hydroxy-2-(3-phenoxyphenyl) acetonitrile), 4-methylmandelonitrile (2-hydroxy-2-(p-tolyl) acetonitrile), 2-chloromandelonitrile (2-(2-chlorophenyl)-2-hydroxyacetonitrile), 3-chloromandelonitrile (2-(3-chlorophenyl)-2-hydroxyacetonitrile), 4-chloromandelonitrile (2-(4-chlorophenyl)-2-hydroxyacetonitrile), 3-nitromandelonitrile (2-hydroxy-2-(3-nitrophenyl)acetonitrile), 3,4-methylenedioxymandelonitrile (2-hydroxy-2-(3,4-methylenedioxyphenyl) acetonitrile), 2,3-methylenedioxymandelonitrile (2-hydroxy-2-(2,3-methylenedioxyphenyl)acetonitrile), 2-benzyl-2-hydroxyacetonitrile and 2-(2-furyl)-2-hydroxyacetonitrile; 2-alkyl-2-hydroxyacetonitrile such as 2-hydroxy-2-methylacetonitrile, 2-hydroxy-2-propylacetonitrile, 2-hydroxy-2-isopropylacetonitrile, 2-butyl-2-hydroxyacetonitrile and 2-cyclohexyl-2-hydroxyacetonitrile; 2,2-dialkyl-2-hydroxyacetonitrile such as 2-ethyl-2-hydroxy-2-methylacetonitrile, 2-butyl-2-hydroxy-2-methylacetonitrile, 2-hydroxy-2-methyl-2-propylacetonitrile, 2-hydroxy-2-isopropyl-2-methylacetonitrile, 2-hydroxy-2-methyl-2-pentylacetonitrile, 2-hydroxy-2-methyl-2-(2-methylpropyl) acetonitrile and 2-hydroxy-2-methyl-2-(3-methylbutyl) acetonitrile; 2-alkyl-2-alkenyl-2-hydroxyacetonitrile such as 2-hydroxy-2-methyl-2-(2-propenyl)acetonitrile and 2-(3-butenyl)-2-hydroxy-2-methylacetonitrile; 2-alkyl-2-(haloalkyl)-2-hydroxyacetonitrile such as 2-(3-chloropropyl)-2-hydroxy-2-methylacetonitrile; 2-(1-(protected amino)alkyl)-2-hydroxyacetonitrile such as 2-(1-alkoxycarbonylamino)-2-cyclohexylethyl)-2-hydroxyacetonitrile; 2-alkylthioalkyl-2-hydroxyacetonitrile such as 2-hydroxy-2-(2-methylthioethyl)acetonitrile; and 2-acyl-2-hydroxyacetonitrile such as 2-hydroxy-2-pivaloilacetonitrile.

An asymmetric divalent group represented by $R^1$ and $R^2$ is not particularly limited, as long as the above groups can convert a carbon atom, to which the groups bind, into an asymmetric carbon, and the examples include norbornane-2-ylidene and 2-norbornene-5-ylidene.

The optically active cyanohydrin used in the third aspect of the present invention may be any of a (S)-form and an (R) form, and this compound can be produced by, for example, such methods as an optical resolution of cyanohydrin obtained by acting alkali cyanide with a corresponding carbonyl compound or its sodium hydrogensulfite adduct; a method of asymmeticly adding hydrogen cyanide to a corresponding carbonyl compound in the presence of enzymes such as (S)-hydroxynitrilelyase and (R)-hydroxynitrilelyase extracted from plants (e.g. *Synthesis*, July 1990, 575–578; *Tetrahedron Letters*, 32, 2605–2608 (1991); Japanese Patent Application filed Nos. 63-219388, 5-317065 and 9-227488); a method of asymmetricly hydrolyzing a material obtained by chemical synthesis of racemic cyanohydrinester, using enzymes (e.g. Japanese Patent Application filed No. 62-65688); and a method of asymmetricly adding hydrogen cyanide to a corresponding carbonyl compound in the presence of enzymes produced by a gene ricombinant microorganism, to which a gene of enzymes such as (S)-hydroxynitrilelyase and (R)-hydroxynitrilelyase is incorporated (e.g. WO98/30711, Japanese Patent Application filed No. 9-227488).

The third aspect of the present invention is characterized in hydrolyzing optically active cyanohydrin, using at most 10 equivalents of mineral acid relative to the optically active cyanohydrin under the condition that maximum temperature when reacting is less than 90° C.

Examples of mineral acid used in the third aspect of the present invention include hydrochloric acid, sulfuric acid, nitric acid, boric acid, phosphoric acid and perchloric acid, hydrochloric acid being preferable.

The usage of more than 10 equivalents of mineral acid relative to optically active cyanohydrin would be economically disadvantageous, resulting in a decrease of yields. However, the extremely low usage of mineral acid would lead to a slow and insufficient reaction, or a reduction in the optical purity of the optically active α-hydroxycarboxylic acid of interest. The preferable usage of mineral acid is 1.5 to 8 equivalents relative to optically active cyanohydrin, and more preferably 2 to 7 equivalents.

A maximum reaction temperature of more than 90° C. would bring on the increase of the generation of by-products and coloration, resulting in the reduction of the optical purity of optically active α-hydroxycarboxylic acid of interest. The maximum reaction temperature is preferably 40 to 80° C., more preferably 45 to 70° C. Where the reaction temperature is less than 40° C., the reaction time is preferably set at 15 hours or less, more preferably 3 hours or less.

A reaction solvent may be used, but such a solvent is not particularly effective and may also reduce yield or optical purity, so it is preferable not to use solvents other than water. At initiation of the reaction, the amount of water contained in a reaction mixture including water in the mineral acid used, is preferably 7 to 50 equivalents relative to optically active cyanohydrin, and more preferably 10 to 40 equivalents.

After reaction, to isolate the α-hydroxycarboxylic acid of interest from the obtained reaction solution (which, at times, may be a slurry), the solution is extracted with an organic solvent and is washed, as needed, and then the solvent is vaporized and exsiccated.

The fourth aspect of the present invention is a method for producing optically active crystalline α-hydroxycarboxylic acid, which comprises crystallizing optically active α-hydroxycarboxylic acid in an aqueous solution. This crystallization may be carried out in the presence of a non-miscible organic solvent, and an example of such an organic solvent includes a hydrocarbon solvent such as benzene, toluene, and o-, m- and p-xylene, n-hexane, n-heptane, n-octane. Where the crystallization is carried out in the presence of a non-miscible organic solvent, the ratio between an aqueous solution and the organic solvent is preferably 1:0.05–1:1. An optically active crystalline α-hydroxycarboxylic acid is deposited by cooling the above optically active α-hydroxycarboxylic acid solution. The cooling temperature is not particularly limited, as long as the temperature is set at, or below, a temperature at which the optically active α-hydroxycarboxylic acid solution to be used becomes a saturated solution, but preferably at 30° C. or less, more preferably at 25° C. or less. It is better to perform the cooling as slowly as possible, preferably at a cooling rate of 0.5° C./min or less.

As optically active α-hydroxycarboxylic acid to be used in the fourth aspect of the present invention, the optically active α-hydroxycarboxylic acid produced by the method of the first, second or third aspect of the present invention may be used. In such a case, crystallization may directly be performed by adding an appropriate amount of water to a reaction solution, without isolating optically active α-hydroxycarboxylic acid from the reaction solution after hydrolysis.

The crystalline α-hydroxycarboxylic acid obtained by the production method of the fourth aspect of the present invention has a higher packing density crystal when compared with the crystals obtained by the previous methods. For example, in a case where optically active 2-chloromandelic acid is used as optically active α-hydroxycarboxylic acid, optically active crystalline 2-chloromandelic acid whose packing density is usually more than 0.5, preferably more than 0.55 and more preferably more than 0.60, can be obtained by the method of the fourth aspect of the present invention, while the packing density of the same crystal obtained by the previous methods is less than 0.50.

According to the first aspect of present invention, it becomes possible to provide a method for easily producing high purity α-hydroxycarboxylic acid, which contains almost no colored substances and by-products. Furthermore, according to the production method of the first aspect of present invention, since the configuration of cyanohydrin does not change before and after hydrolysis, even though optically active cyanohydrin is used, a corresponding optically active α-hydroxycarboxylic acid can be obtained, while maintaining its optical purity.

According to the second and third aspects of the present invention, optically active α-hydroxycarboxylic acid can be produced with high yield and high purity.

According to the fourth aspect of the present invention, optically active crystalline α-hydroxycarboxylic acid can be obtained with high packing density and high optical purity.

This specification includes part or all of the contents as disclosed in the specifications of Japanese Patent Applications Nos. 2000-166382, 2000-171186 and 2000-350695, which are the bases of the priority claim of the present application.

DETAILED DESCRIPTION OF THE PREFERRED EMBODIMENTS

The present invention is further described in the following examples. The example is provided for illustrative purposes only, and is not intended to limit the scope of the invention.

EXAMPLE 1

25.2 g (0.150 mol) of (R)-2-chloromandelonitrile whose optical purity is 98% e.e., 46.9 g of 35% hydrochloric acid (HCl 0.450 mol) and 7.56 g of toluene were placed into a 100 ml flask and stirred at room temperature for 1 hour, followed by reaction with heating at 70° C. for 4 hours. After cooling to room temperature and leaving at rest, the upper phase, toluene was removed. 50 g of ethyl acetate was added to the remaining aqueous phase and mixed in a separatory funnel, while shaking, followed by separation of the organic phase from the water phase. The water phase was extracted with 50 g of ethyl acetate, and the obtained organic phase was mixed with the previous organic phase, then the mixture was washed with 15 g of water. The thus obtained solution containing the (R)-2-chloromandelic acid was exsiccated under a reduced pressure, and then washed with 25 g of toluene and dried to obtain 26.9 g of (R)-2-chloromandelic acid. The optical purity was 96.6% (e.e.) The yield of the obtained (R)-2-chloromandelic acid was 94.4%.

EXAMPLE 2

The same reaction as in Example 1 was carried out to produce (R)-2-chloromandelic acid, with the exception that the amount of toluene was set at 25.2 g.

EXAMPLE 3

The same reaction as in Example 1 was carried out to produce (R)-2-chloromandelic acid, with the exception that benzene was used instead of toluene.

EXAMPLE 4

The same reaction as in Example 1 was carried out to produce (R)-2-chloromandelic acid, with the exception that p-xylene was used instead of toluene.

CONTROL EXAMPLE 1

The same reaction as in Example 1 was carried out to produce (R)-2-chloromandelic acid, with the exception that toluene was not added.

The results of Examples 1 to 4 and Control example 1 are shown in the following Table 1.

TABLE 1

| No. | Hydrocarbon solvents (ratio of weight to cyanohydrin) | Coloration of reaction solution | Yield of R-2CMA (%) | Purity of carboxylic acid (%) | Optical purity (% e.e.) |
|---|---|---|---|---|---|
| Example 1 | toluene (0.3) | light orange | 94.4 | 99.0 | 96.6 |
| Example 2 | toluene (1.0) | extremely light yellow | 93.6 | 99.3 | 96.7 |
| Example 3 | benzene (0.3) | light orange | 94.1 | 99.1 | 96.6 |
| Example 4 | p-xylene (0.3) | light orange | 93.8 | 98.8 | 96.4 |
| Control 1 | none | dark reddish brown | 93.6 | 96.5 | 96.2 |

R-2CMA: (R)-2-chloromandelic acid

PREPARATION EXAMPLE 1

Preparation of S-hydroxynitrilelyase
(Preparation of S-hydroxynitrilelyase)

According to genetic engineering procedures, S-hydroxynitrilelyase was prepared using a yeast *saccharonyces cerevisae* as a host. That is to say, according to standard techniques, total mRNA was extracted from the leaf of *Manihot utilissima*. Then, using the obtained mRNA as a template, cDNA synthesis was carried out to produce cDNA. Meanwhile, based on the sequence of S-hydroxynitrilelyase gene from *Manihot utilissima* described in a reference (*Arch. Biochem. Biophys.* 311, 496–502 (1994)), the following primers were synthesized. With regard to the synthesized DNA of each of the following SEQ ID NOS: 1 and 2, a sequence listing is provided.

```
Sense primer:
                                  (SEQ ID NO: 1)
ggggaattcatggtaactgcacattttgttctgattc Antisense primer:
                                  (SEQ ID NO: 2)
ggggtcgacctcacggattagaagccgccg
```

With the synthesized primers, PCR (90° C., 30 seconds; 55° C., 30 seconds; 72° C., 60 seconds; 35 cycles in total) was carried out using the above cDNA as a template, to obtain a S-hydroxynitrilelyase gene. The analysis of the gene sequence showed that the sequence of the S-hydroxynitrilelyase gene matched with the sequence shown in the reference.

Subsequently, the obtained PCR fragments were inserted between the promoter and terminator of an expression vector, YEp352-GAP, to obtain a yeast episomic expression vector, YEp352-GC. This vector was transformed into a yeast *saccharomyces cerevisae* Inv-Sc1 strain according to standard techniques, and then the obtained strains were cultured on a minimum selective medium, which did not contain uracil, so that recombinant yeast YEp352-GC-S2 strains containing an expression vector YEp352-GC were obtained.

Then, the obtained recombinant yeast YEp352-GC-S2 strains were cultured in a YNBDCas liquid medium (6.7 g/L Yeast nitrogen hase without amino acid (Difco), 20 g/L glucose, 20 g/L casamino acid, 40 mg/mL L-tryptophan) for 24 hours to produce S-hydroxynitrilelyase in a cell thereof. Cells were collected from a recombinant cell culture solution by centrifugation, and then the obtained cell bodies were crushed by bead mill. The crushed cell bodies-containing solution was centrifuged to prepare a crude enzyme solution. The solution was roughly purified by ammonium sulfate fractionation, and the obtained solution was used as a S-hydroxynitrilelyase solution for the following experiments.

(Immobilization of S-hydroxynitrilelyase)

The above-prepared S-hydroxynitrilelyase was immobilized to Micro Bead Silica Gel 300A (Fuji Silysia Chemical Ltd.) The immobilization of enzyme was carried out by adding 200 g of carrier to 1.0L of S-hydroxynitrilelyase solution (activity: 64 U/ml, 0.02M HEPES-Na buffer (pH 6.0)), stirring the mixture at 4° C. for 24 hours, and performing the adsorption immobilization of enzyme protein to the carrier.

($1^{st}$ Step: Synthesis of Optically Active Cyanohydrin with Immobilized Enzyme)

EXAMPLE 1'

200 g of immobilized enzyme, 1.2L of t-butylmethyl ether (tBME) saturated with 10 mM phosphate buffer (pH 5.5), 127.2 g (2.0 mol) of benzaldehyde and 49.2 g (3.0 mol) of hydrocyanic acid were placed into a 2L-volume flask, and stirred at 20° C. for 1 hour. After reaction, the amount and optical purity of the obtained cyanohydrin were determined by analyzing the reaction solution by HPLC.

EXAMPLE 2'

The same reaction as in Example 1' was carried out, with the exception that ethyl acetate was used as a solvent, instead of tBME.

EXAMPLE 3'

5.0 L of 25 weight % methanol solution containing 0.1M benzaldehyde, 0.3M hydrocyanic acid and 0.05M sodium acetate, and 50 g of immobilized enzyme were placed into a 5L-volum flask, followed by the same reaction as in Example 1'.

REFERENCE EXAMPLE

The same reaction as in Example 1' was carried out, with the exception that hexane was used as a solvent, instead of tBME.

The results of the above reactions are shown in Table 2.

TABLE 2

| | Solvent | Invert ratio (%) | Optical purity (% ee) |
|---|---|---|---|
| Example 1' | tBME | 98 | more than 99.9 |
| Example 2' | ethyl acetate | 97 | more than 99.9 |
| Example 3' | methanol/water | 96 | 99.8 |
| Reference example | hexane | 96 | 99.8 |

($2^{nd}$ Step: Hydrolysis)

EXAMPLE 1A

After the reaction solution of Example 1' was filtrated to remove immobilized enzyme, 2.3 g of para-toluene sulfonate monohydrate was added thereto and shaken. After that, one quarter of the obtained reaction solution (which corresponds to 0.5 mol of initiation material) was concentrated with an evaporator until the amount of tBME became 2 weight %, and transferred into a 300 mL flask with a reflux condenser. 156 g of 35% hydrochloric acid (HCl, 1.5 mol) was added thereto, and stirred at room temperature for 1 hour, followed by further stirring at 70° C. for 5 hours. After cooling the mixture to room temperature, 175 g of ethyl acetate was added thereto and mixed in a separatory funnel, while shaking, the organic phase was separated from water phase. Water phase was extracted with 175 g of ethyl acetate again, and the obtained organic phase was mixed with the previous organic phase, then the mixture was washed with 50 g of water. Such obtained organic phase was exsiccated under a reduced pressure, and then washed with 80 g of toluene and dried to obtain 71.7 g of s-mandelic acid. The purity of s-mandelic acid (including R-form) was determined to be 98.8%, and the optical purity was 99.0% (e.e.) (HPLC).

EXAMPLE 1B

The same reaction as in Example 1A was carried out, with the exception that the amount of tBME was set at 5 weight %.

EXAMPLE 2A

The reaction solution of Example 1' was filtrated to remove immobilized enzyme, and then using one quarter of the obtained reaction solution, the same reaction as in Example 1A was carried out with the amount of ethyl acetate of 3 weight % in material.

EXAMPLE 2B

The same reaction as in Example 2A was carried out, with the exception that the amount of ethyl acetate was set at 8 weight %.

EXAMPLE 3A

The reaction solution obtained in Example 3' was filtrated, and 0.58 g of para-toluene sulfonate monohydrate was added thereto and shaken. The whole amount of the obtained reaction solution was concentrated until the amount of methanol became 5 weight %, and then the same reaction as in Example 1A was carried out.

REFERENCE EXAMPLE

The reaction solution obtained in Reference example of the $1^{st}$ step was filtrated to remove immobilized enzyme, and then using one quarter of the obtained reaction solution, the same reaction as in Example 1A was carried out with the amount of hexane of 15 weight % in material.

CONTROL EXAMPLES 1' TO 3'

The same reaction as in Examples was carried out, with the exception that the amount of solvent remaining in the material for hydrolysis was changed.

The results of the hydrolysis reactions are shown in Table 3.

TABLE 3

| No. | Amount of solvent (wt %) | Yield of carboxylic acid (%) | Optical purity (% ee) |
|---|---|---|---|
| Example 1A | tBME (2) | 95 | 99.0 |
| Example 1B | tBME (5) | 93 | 98.3 |
| Example 2A | ethyl acetate (3) | 94 | 98.8 |
| Example 2B | ethyl acetate (8) | 92 | 97.9 |
| Example 3' | methanol (5) | 95 | 97.1 |
| Reference example | hexane (15) | 96 | 98.5 |
| Control example 1' | tBME (15) | 86 | 89.0 |
| Control example 2A | ethyl acetate (12) | 89 | 86.4 |
| Control example 2B | ethyl acetate (20) | 85 | 84.0 |
| Control example 3' | methanol (15) | 90 | 92.5 |

Note:
The above yield of carboxylic acid was determined by, first, obtaining the number of moles from the yield and HPLC purity, and then calculating the obtained value with the number of moles of cyanohydrin (including R-form) obtained in the $1^{st}$ step.

EXAMPLE 1"

25.2 g (0.150 mol) of (R)-2-chloromandelonitrile and 46.9 g (HCl 0.450 mol) of 35% hydrochloric acid were placed into a 100 ml flask. After stirring at room temperature for 1 hour, the mixture was heated to 50° C. followed by reaction for 15 hours. After cooling the reactant to room temperature, 50 g of ethyl acetate was added thereto and mixed in a separatory funnel, while shaking, thereby separating the organic phase from aqueous phase. The aqueous phase was extracted with 50 g of ethyl acetate, and the obtained organic phase was mixed with the previous organic phase, then the mixture was washed with 15 g of water. The thus obtained solution containing (R)-2-chloromandelic acid of interest was exsiccated under a reduced pressure, and then washed with 25 g of toluene and dried to obtain 26.5 g of (R)-2-chloromandelic acid. The purity of (R)-2-chloromandelic acid by HPLC was 99.0%, and the optical purity was 97.0% (e.e.) The yield of the obtained (R)-2-chloromandelic acid was 94%, and the packing density was 0.49.

EXAMPLES 2" AND 3", AND CONTROL EXAMPLES 1" AND 2"

(R)-2-chloromandelic acid was produced by the same method as described in Example 1", with the exception that the amount of 35% hydrochloric acid used, reaction temperature and reaction time were changed.

The reaction conditions and results are shown in Table 4.

Each of the maximum reaction temperature in Examples 1" to 3" and Control examples 1" and 2" was 50° C., 80° C., 50° C., 100° C. and 50° C., respectively.

TABLE 4

| No. | Acid (Usage molar ratio) | Reaction temperature & Reaction time | Reaction yield (%) of carboxylic acid | Purity (%) of carboxylic acid | Optical purity (% e.e.) | (R)-2-CIMA* yield (%) |
|---|---|---|---|---|---|---|
| Example 1" | 35% HCl (3.0) | RT* 1 h 50° C. 15 h | 98 | 99.0 | 97.0 | 94 |
| Example 2" | 35% HCl (3.0) | RT* 1 h 80° C. 3 h | 97 | 98.5 | 92.6 | 87 |
| Example 3" | 35% HCl (6.0) | RT* 1 h 50° C. 12 h | 98 | 99.3 | 98.0 | 94 |
| Control example 1" | 35% HCl (3.0) | RT* 1 h 100° C. 2 h | 93 | 93.2 | 59.5 | 70 |
| Control example 2" | 35% HCl (20) | RT* 1 h 50° C. 12 h | 96 | 99.0 | 96.6 | 68 |

*RT: room temperature
*(R)-2-CIMA: (R)-2-chloromandelic acid

CRYSTALLIZATION EXAMPLE

Hydrolysis was carried out at 5 times the scale of Example 1". That is, 126 g (0.75 mol) of (R)-2-chloromandelonitrile and 234.5 g (HCl 2.25 mol) of 35% hydrochloric acid were placed into a 50 ml flask, and the mixture was stirred at room temperature for 1 hour. Then, the mixture was heated to 50° C., and reaction was performed for 15 hours.

After completion of the reaction, 120 g of water was added to the reaction solution, followed by stirring at 50° C. for 10 minutes to homogenize the solution. This solution was divided into 5 equal portions at a temperature of 50° C., then crystallization was carried out for each portion under different conditions. Each crystallization example is shown below.

EXAMPLE 1S

The reaction solution, into which water was added, was cooled to 20° C. at constant cooling rate for 90 minutes followed by keeping at 20° C. for 2 hours, and then the solution was filtrated. The obtained crystal was washed with 10 g of water and then with 15 g of toluene, followed by drying, thereby obtaining 25.3 g of (R)-2-chloromandelic acid. The purity of (R)-2-chloromandelic acid was determined to be 99.3% by HPLC, the optical putiry being 98.7% (ee). The yield of the obtained (R)-2-chloromandelic acid was 89.0%. The packing density of the obtained (R)-2-chloromandelic acid was determined to be 0.58 by the method described later.

EXAMPLE 2S

The same reaction as in Example 1S was carried out, with the exception that cooling was initiated after adding 15 g of toluene. The yield of (R)-2-chloromandelic acid was 24.6 g. The purity of (R)-2-chloromandelic acid was 99.6%, the optical purity being 99.5% (ee). The yield of the obtained (R)-2-chloromandelic acid was 87.2%, the packing density being 0.62.

EXAMPLE 3S

The same reaction as in Example 2S was carried out, with the exception that cooling time was set at 30 minutes. The yield of (R)-2-chloromandelic acid was 24.8 g. The purity of (R)-2-chloromandelic acid was 99.4%, the optical purity being 99.3% (ee). The yield of the obtained (R)-2-chloromandelic acid was 87.7%, the packing density being 0.60.

EXAMPLE 4S

The same reaction as in Example 2S was carried out, with the exception that the reaction solution was cooled to 5° C. The yield of (R)-2-chloromandelic acid was 24.9 g. The purity of (R)-2-chloromandelic acid was 99.3%, the optical purity being 99.1% (ee). The yield of the obtained (R)-2-chloromandelic acid was 88.0%, the packing density being 0.63.

EXAMPLE 5S

The same reaction as in Example 2S was carried out, with the exception that p-xylene was used instead of toluene. The yield of (R)-2-chloromandelic acid was 24.8 g. The purity of (R)-2-chloromandelic acid was 99.4%, the optical purity being 99.1% (ee). The yield of the obtained (R)-2-chloromandelic acid was 87.6%, the packing density being 0.62.

(Determination of Packing Density)

About 20 g of crystal was naturally dropped through a 20 mm-diameter funnel into a 50 mL graduated cylinder, and the packing density of the crystal was calculated by measuring the weight and volume of the crystal.

TABLE 5

| | hydrocarbon | Final temperature (° C.) | cooling time (min) | Yield of products (%) | Purity (%) | Optical purity (% ee) | Filling density (g/cm³) |
|---|---|---|---|---|---|---|---|
| Example 1S | none | 20 | 90 | 89.0 | 99.3 | 98.7 | 0.58 |
| Example 2S | toluene | 20 | 90 | 87.2 | 99.6 | 99.5 | 0.62 |
| Example 3S | toluene | 20 | 30 | 87.7 | 99.4 | 99.3 | 0.60 |
| Example 4S | toluene | 5 | 90 | 88.0 | 99.3 | 99.1 | 0.63 |
| Example 5S | p-xylene | 20 | 90 | 87.6 | 99.4 | 99.1 | 0.62 |

All the publications, patents and patent applications cited herein are incorporated herein by reference in their entirely.

What is claimed is:

1. A method of hydrolyzing an optically pure cyanohydrin to its corresponding α-hydroxycarboxylic acid comprising, combining in a reaction mixture:
the optically pure cyanohydrin;
water;
at least one mineral acid that catalyzes the hydrolysis; and
at least one hydrocarbon solvent;
wherein the reaction mixture comprises less than 10% by weight of an organic solvent other than the at least one hydrocarbon solvent.

2. The method of claim 1, wherein the reaction mixture comprises less than 5% by weight of an organic solvent other than the at least one hydrocarbon solvent.

3. The method of claim 1, wherein the amount of water in the reaction mixture ranges from 7 equivalents to 50 equivalents relative to the cyanohydrin.

4. The method of claim 1, wherein the amount of water in the reaction mixture ranges from 10 equivalents to 40 equivalents relative to the cyanohydrin.

5. The method of claim 1, wherein the amount of the at least one mineral acid in the reaction mixture is less than 10 equivalents relative to the cyanohydrin.

6. The method of claim 1, wherein the amount of the at least one mineral acid in the reaction mixture ranges from 2 equivalents to 7 equivalents relative to the cyanohydrin.

7. The method of claim 1, wherein the at least one mineral acid is selected from hydrochloric acid, sulfuric acid, nitric acid, boric acid, phosphoric acid, and perchioric acid.

8. The method of claim 1, wherein the at least one hydrocarbon solvent is selected from a saturated or unsaturated linear or branched chain hydrocarbon of 5 to 16 carbon atoms, a saturated or unsaturated cyclic hydrocarbon with or without a side chain of 6 to 16 carbon atoms, and a saturated or unsaturated linear or branched chain hydrocarbon substituted with a cyclic hydrocarbon of 5 to 16 carbon atoms.

9. The method of claim 1, wherein the at least one hydrocarbon solvent comprises an aromatic hydrocarbon of 6 to 16 carbon atoms.

10. The method of claim 9, wherein the aromatic hydrocarbon is selected from benzene, toluene, and xylene.

11. The method of claim 1, wherein the maximum temperature of the hydrolysis reaction ranges from 40° C. to 90° C.

12. A. The method of claim 1, wherein the maximum temperature of the hydrolysis reaction ranges from 50° C. to 80° C.

13. The method of claim 1, further comprising separating and removing the hydrocarbon solvent phase from the reaction mixture following the hydrolysis reaction.

14. A method of hydrolyzing an optically pure cyanohydrin to its corresponding α-hydroxycarboxylic acid comprising, combining in a reaction mixture:
the optically pure cyanohydrin;
water wherein the amount of water comprising the reaction mixture ranges from 10 equivalents to 40 equivalents relative to the optically pure cyanohydrin;
at least one mineral acid selected from hydrochloric acid, sulfuric acid, nitric acid, boric acid, phosphoric acid, and perchloric acid, wherein the amount of the at least one mineral acid in the reaction mixture ranges from 2 equivalents to 7 equivalents relative to the optically pure cyanohydrin; and
at least one aromatic solvent selected from beuzene, toluene, and xylene;
wherein the reaction mixture comprises less than 5% by weight of an organic solvent other than the hydrocarbon solvent, and
wherein the maximum temperature of the hydrolysis reaction ranges from 50° C. to 80° C.

15. A method of crystallizing optically pure α-hydroxycarboxylic acid in an aqueous solution comprising:
suspending the optically pure α-hydroxycarboxylic acid in an aqueous solution; and cooling the aqueous solution to a temperature of less than 30° C. at a rate of 0.5° C./min or less, to produce crystalline optically pure α-hydroxycarboxylic acid.

16. The method of claim 15, wherein the aqueous solution comprises at least one non-miscible organic solvent.

17. The method of claim 16, wherein the at least one non-miscible organic solvent is selected from at least one hydrocarbon solvent.

18. The method of claim 17, wherein the at least one hydrocarbon solvent is selected from benzene, toluene, o-xylene, m-xylene, p-xylene, n-hexane, n-heptane, and n-octane.

19. The method of claim 16, wherein the ratio of the volume of the aqueous solution to the volume of the non-miscible organic solvent ranges from 1:0.05 to 1:1.

20. The method of claim 15, wherein the crystalline optically pure α-hydroxycarboxylic acid exhibits a packing density of at least 0.5 g/cm$^3$.

21. The method of claim 15, wherein the crystalline optically aetwe pure α-hydroxycarboxylic acid exhibits a packing density of at least 0.6 g/cm$^3$.

22. The method of claim 15, wherein the optically pure α-hydroxycarboxylic acid is produced according to the method of claim 20.

23. The method of claim 15, wherein the optically pure α-hydroxycarboxylic acid is produced according to the method of claim 14.

* * * * *

UNITED STATES PATENT AND TRADEMARK OFFICE
CERTIFICATE OF CORRECTION

PATENT NO. : 6,864,389 B2
DATED : March 8, 2005
INVENTOR(S) : Norimasa Okuda et al.

It is certified that error appears in the above-identified patent and that said Letters Patent is hereby corrected as shown below:

Column 33,
Line 56, "perchioric" should read -- perchloric --.

Column 34,
Line 34, before "The method", delete "A.".
Line 55, "beuzene," should read -- benzene, --.

Column 36,
Line 5, after "optically", delete "aetwe".
Line 10, "claim 20." should read -- claim 1. --.

Signed and Sealed this

Twenty-eighth Day of June, 2005

JON W. DUDAS
*Director of the United States Patent and Trademark Office*